United States Patent
Ducray et al.

(10) Patent No.: US 6,673,820 B2
(45) Date of Patent: Jan. 6, 2004

(54) AMINOHETEROCYCLYLAMIDES AS PESTICIDES AND ANTIPARASITIC AGENTS

(75) Inventors: Pierre Ducray, Saint-Louis (FR); Jacques Bouvier, Neuchatel (CH); Maurizio Schwarzenbach, Ramlinsburg (CH)

(73) Assignee: Novartis Animal Health US, Inc., Greensboro, NC (US)

( * ) Notice: Subject to any disclaimer, the term of this patent is extended or adjusted under 35 U.S.C. 154(b) by 0 days.

(21) Appl. No.: 10/148,644

(22) PCT Filed: Nov. 30, 2000

(86) PCT No.: PCT/EP00/12064

§ 371 (c)(1),
(2), (4) Date: May 31, 2002

(87) PCT Pub. No.: WO01/40223

PCT Pub. Date: Jun. 7, 2001

(65) Prior Publication Data

US 2003/0148890 A1 Aug. 7, 2003

(30) Foreign Application Priority Data

Dec. 2, 1999 (CH) .............................. 2207/99

(51) Int. Cl.⁷ .................. C07D 417/12; C07D 409/12; A01N 43/00
(52) U.S. Cl. ................. 514/363; 514/363; 548/100; 548/125; 548/128
(58) Field of Search ................. 548/100, 125, 548/128; 514/363

(56) References Cited

U.S. PATENT DOCUMENTS 4,966,908 A * 10/1990 Eckhardt et al. ............ 514/340

FOREIGN PATENT DOCUMENTS

| DE | 24 34 922 | 1/1975 |
|---|---|---|
| EP | 0 623 282 A1 | 5/1994 |
| GB | 1 226 913 | 6/1909 |
| GB | 2 331 748 | 6/1999 |
| JP | 2000226389 | 8/2000 |

* cited by examiner

*Primary Examiner*—Sabiha Qazi
(74) *Attorney, Agent, or Firm*—Michael U. Lee; John W. Kung

(57) ABSTRACT

The invention relates to novel compounds of the general formula:

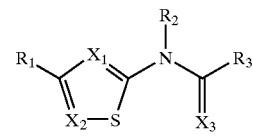

in which $R_1$ is hydrogen, halogen, $C_1$–$C_6$alkyl, $C_1$–$C_6$alkoxy, $C_1$–$C_6$haloalkyl or unsubstituted or mono- to pentasubstituted phenyl, where the substituents are selected from the group consisting of $C_1$–$C_6$alkyl, $C_1$–$C_6$haloalkyl, $C_1$–$C_6$alkoxy, aryloxy, halogen, cyano and nitro, where, if the number of substituents exceeds 1, the substituents can be identical or different; $R_2$ is hydrogen, $C_1$–$C_6$alkyl, ($C_1$–$C_6$alkylene)phenyl, pyridyl, $COOR_6$, $CONR_7R_8$, $COR_6$, allyl or $CH_2$—O—$R_6$; $R_3$ is unsubstituted or substituted heterocyclyl, where the substituents are in each case selected from the group consisting of unsubstituted or substituted phenyl, where the substituents are selected from the group consisting of $C_1$–$C_6$alkyl, $C_1$–$C_6$alkoxy, halogen, cyano and nitro, where, if the number of substituents exceeds 1, the substituents can be identical or different, benzyl, $C_1$–$C_6$alkyl, $C_1$–$C_6$haloalkyl, $C_1$–$C_6$alkoxy, aryloxy, halogen, cyano, hydroxyl, amino and nitro, where, if the number of substituents exceeds 1, the substituents can be identical or different; $R_6$ is $C_1$–$C_6$alkyl, phenyl or benzyl; $R_7$ and $R_8$ independently of one another are hydrogen or $C_1$–$C_6$alkyl; $X_1$ and $X_2$ are each N; and $X_3$ is O or S. The novel compounds have advantageous pesticidal properties and are particularly suitable for controlling pests in domestic and useful animals.

5 Claims, No Drawings

AMINOHETEROCYCLYLAMIDES AS PESTICIDES AND ANTIPARASITIC AGENTS

This is the national stage application of international application number PCT/EP00/12064 filed on Nov. 30, 2000.

The present invention relates to novel substituted aminoheterocyclylamides of the formula

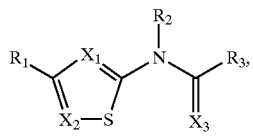

in which
- $R_1$ is hydrogen, halogen, $C_1$–$C_6$alkyl, $C_1$–$C_6$alkoxy, $C_1$–$C_6$haloalkyl or unsubstituted or mono- to pentasubstituted phenyl, where the substituents are selected from the group consisting of $C_1$–$C_6$alkyl, $C_1$–$C_6$haloalkyl, $C_1$–$C_6$alkoxy, aryloxy, halogen, cyano and nitro, where, if the number of substituents exceeds 1, the substituents can be identical or different;
- $R_2$ is hydrogen, $C_1$–$C_6$alkyl, ($C_1$–$C_6$alkylene)phenyl, pyridyl, $COOR_6$, $CONR_7R_8$, $COR_6$, allyl or $CH_2$—O—$R_6$;
- $R_3$ is unsubstituted or substituted heterocyclyl, where the substituents are in each case selected from the group consisting of unsubstituted or substituted phenyl, where the substituents are selected from the group consisting of $C_1$–$C_6$alkyl, $C_1$–$C_6$alkoxy, halogen, cyano and nitro, where, if the number of substituents exceeds 1, the substituents can be identical or different, benzyl, $C_1$–$C_6$alkyl, $C_1$–$C_6$haloalkyl, $C_1$–$C_6$alkoxy, aryloxy, halogen, cyano, hydroxyl, amino and nitro, where, if the number of substituents exceeds 1, the substituents can be identical or different;
- $R_6$ is $C_1$–$C_6$alkyl, phenyl or benzyl;
- $R_7$ and $R_8$ independently of one another are hydrogen or $C_1$–$C_6$alkyl;
- $X_1$ is N or C(CN);
- $X_2$ is N, C(CN), C($COOR_6$), C($COR_6$), C($SOR_6$), C($CONR_7R_8$) or C($NO_2$); and
- $X_3$ is O or S;
- to their preparation and to their use for controlling pests, and furthermore to pesticides comprising at least one of these compounds.

Substituted aminoheterocyclylamides having pesticidal action are described, for example, in DE 197 27 162. However, the active compounds actually disclosed in this publication cannot always meet the requirements with respect to activity efficacy and spectrum. Accordingly, there is a need for active compounds having improved pesticidal properties. It has now been found that the aminoheterocyclylamides of the formula I have excellent pesticidal properties, in particular against endoparasites.

The alkyl groups mentioned in the definitions of substituents can be straight-chain or branched and are, for example, methyl, ethyl, n-propyl, isopropyl, n-butyl, sec-butyl, isobutyl, tert-butyl, pentyl and hexyl, and their branched isomers.

Corresponding alkylene groups can likewise be straight-chain or branched and are, for example, methylene, ethylene, n-propylene, isopropylene, n-butylene, sec-butylene, isobutylene, tert-butylene, pentylene and hexylene, and their branched isomers.

Halogen is generally fluorine, chlorine, bromine or iodine. This also applies to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy and tert-butoxy, and the isomers pentyloxy and hexyloxy; preferably methoxy and ethoxy.

Aryloxy is phenoxy or naphthyloxy, preferably phenoxy.

Heterocyclyl is an aromatic 5- or 6-membered cyclic group which may be benzo-fused and which contains at least one heteroatom selected from the group consisting of oxygen, nitrogen and sulfur. Typical representatives are, for example, pyridyl, pyrryl, furyl, thienyl, imidazolyl, pyrazolyl, benzofuryl, benzothienyl, isoxazolyl, oxazolyl, thiazolyl and indolyl.

Preferred compounds of the formula I are those in which
- $R_1$ is halogen, $C_1$–$C_6$alkoxy, $C_1$–$C_6$haloalkyl or phenyl;
- $R_2$ is hydrogen, $C_1$–$C_6$alkyl, ($C_1$–$C_6$alkylene)phenyl or pyridyl;
- $R_3$ is unsubstituted or substituted heterocyclyl, where the substituents are in each case selected from the group consisting of unsubstituted or substituted phenyl, where the substituents are selected from the group consisting of $C_1$–$C_6$alkoxy, halogen, cyano and nitro, where, if the number of substituents exceeds 1, the substituents can be identical or different, benzyl, $C_1$–$C_6$alkyl, $C_1$–$C_6$haloalkyl, $C_1$–$C_6$alkoxy, aryloxy, halogen, cyano, hydroxyl, amino and nitro, where, if the number of substituents exceeds 1, the substituents can be identical or different;
- $X_1$ is N or C(CN);
- $X_2$ is N or C(CN); and
- $X_3$ is O or S.

Particularly preferred embodiments of the compounds of the formula I are:
(1) a compound of the formula I in which $R_1$ is halogen, $C_1$–$C_6$haloalkyl or phenyl; preferably fluorine, chlorine, $C_1$–$C_4$haloalkyl or phenyl; particularly preferably chlorine, $C_1$–$C_2$haloalkyl or phenyl; very particularly preferably chlorine, trichloromethyl or phenyl;
(2) a compound of the formula I in which $R_2$ is hydrogen, $C_1$–$C_4$alkyl or ($C_1$–$C_4$alkylene)phenyl; preferably hydrogen or ($C_1$–$C_2$alkylene)phenyl; particularly preferably hydrogen;
(3) a compound of the formula I in which $R_3$ is unsubstituted or substituted pyrazolyl or unsubstituted or substituted pyridyl, where the substituents are in each case selected from the group consisting of unsubstituted or substituted phenyl, where the substituents are selected from the group consisting of $C_1$–$C_6$alkoxy, halogen, cyano and nitro, where, if the number of substituents exceeds 1, the substituents can be identical or different, benzyl, $C_1$–$C_6$alkyl, $C_1$–$C_6$haloalkyl, $C_1-C_6$alkoxy, aryloxy, halogen, cyano, hydroxyl, amino and nitro, where, if the number of substituents exceeds 1, the substituents can be identical or different;

preferably substituted pyrazolyl or substituted pyridyl, where the substituents are in each case selected from the group consisting of substituted phenyl, where the substituents are selected from the group consisting of $C_1-C_2$alkoxy, halogen and nitro, where, if the number of substituents exceeds 1, the substituents can be identical or different, $C_1-C_4$alkyl, $C_1-C_4$haloalkyl, $C_1-C_4$alkoxy, halogen and nitro, where, if the number of substituents exceeds 1, the substituents can be identical or different; particularly preferably substituted pyrazolyl, where the substituents are selected from the group consisting of substituted phenyl, where the substituents are selected from the group consisting of methoxy, chlorine, fluorine and nitro, where, if the number of substituents exceeds 1, the substituents can be identical or different, $C_1-C_4$alkyl, $C_1-C_2$haloalkyl, chlorine and fluorine, where, if the number of substituents exceeds 1, the substituents can be identical or different; very particularly preferably substituted pyrazolyl, where the substituents are selected from the group consisting of substituted phenyl, where the substituents are selected from the group consisting of methoxy, chlorine and fluorine, where, if the number of substituents exceeds 1, the substituents can be identical or different, $C_1-C_2$alkyl and $C_1-C_2$haloalkyl, where, if the number of substituents exceeds 1, the substituents can be identical or different;

(4) a compound of the formula I in which $X_1$ and $X_2$ are N;

(5) a compound of the formula I in which $X_3$ is O;

(6) a compound of the formula I in which $R_1$ is halogen, $C_1-C_6$haloalkyl or phenyl; $R_2$ is hydrogen, $C_1-C_4$alkyl or $(C_1-C_4$alkylene)phenyl; $R_3$ is substituted pyrazolyl or substituted pyridyl, where the substituents are in each case selected from the group consisting of substituted phenyl, where the substituents are selected from the group consisting of $C_1-C_2$alkoxy, halogen and nitro, where, if the number of substituents exceeds 1, the substituents can be identical or different, $C_1-C_4$alkyl, $C_1-C_4$haloalkyl, $C_1-C_4$alkoxy, halogen and nitro, where, if the number of substituents exceeds 1, the substituents can be identical or different; $X_1$ and $X_2$ are N; and $X_3$ is O;

(7) a compound of the formula I in which $R_1$ is fluorine, chlorine, $C_1-C_4$haloalkyl or phenyl;

$R_2$ is hydrogen or $(C_1-C_2$alkylene)phenyl; $R_3$ is substituted pyrazolyl, where the substituents are selected from the group consisting of substituted phenyl, where the substituents are selected from the group consisting of methoxy, chlorine, fluorine and nitro, where, if the number of substituents exceeds 1, the substituents can be identical or different, $C_1-C_4$alkyl, $C_1-C_2$haloalkyl, fluorine and chlorine, where, if the number of substituents exceeds 1, the substituents can be identical or different; $X_1$ and $X_2$ are N; and $X_3$ is O;

(8) a compound of the formula I in which $R_1$ is chlorine, trichloromethyl or phenyl; $R_2$ is hydrogen; $R_3$ is substituted pyrazolyl, where the substituents are selected from the group consisting of substituted phenyl, where the substituents are selected from the group consisting of methoxy, chlorine and fluorine, where, if the number of substituents exceeds 1, the substituents can be identical or different, $C_1-C_2$alkyl and $C_1-C_2$haloalkyl, where, if the number of substituents exceeds 1, the substituents can be identical or different; $X_1$ and $X_2$ are N; and $X_3$ is O.

The invention also provides a process for preparing the compounds of the formula I and, if appropriate, their enantiomers, which comprises, for example, reacting a compound of the formula

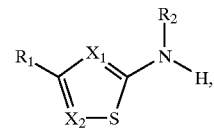

II which is known or can be prepared analogously to corresponding known compounds and in which $R_1$, $R_2$, $X_1$ and $X_2$ are as defined for formula I, with a compound of the formula

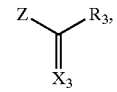

III which is known or can be prepared analogously to corresponding known compounds and in which $X_3$ and $R_3$ are as defined for formula I and Z is a leaving group, if appropriate in the presence of a basic catalyst, and in each case, if desired, converting a compound of the formula I obtainable by the process or in another manner, or an enantiomer thereof, into another compound of the formula I or an enantiomer thereof, separating an enantiomer mixture obtainable by the process and isolating the desired enantiomer.

Suitable leaving groups are halogen, $C_1-C_6$alkoxy and hydroxyl, preferably chlorine.

Suitable bases for facilitating the reaction are, for example, trialkylamines, basic heterocycles or phosphines. Examples which may be mentioned are triethylamine, diisopropylethylamine, pyridine, 4-(N,N-dimethylamino) pyridine, quinuclidine, 1,5-diazabicyclo[5.4.0]undec-5-ene (DBU) and triphenylphosphine. Preference is given to diisopropylethylamine.

The reactants can be reacted with one another as such, i.e. without addition of a solvent or diluent, for example in the melt. However, in most cases the addition of an inert solvent or diluent or a mixture thereof is advantageous. Examples of such solvents or diluents which may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, carbon tetrachloride, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; amides, such as N,N-dimethylformamide, N,N-diethylformamide, N,N-dimethylacetamide, N-methylpyrrolidone or hexamethylphosphoric triamide; nitriles, such as acetonitrile or propionitrile; and sulfoxides, such as dimethyl sulfoxide. If the reaction is carried out in the presence of a base, it is also possible for bases such as triethylamine, pyridine, N-methylmorpholine or N,N-diethylaniline, employed in excess, to serve as solvent or diluent. Preference is given to using halogenated hydrocarbons, in particular dichloromethane.

The reaction is advantageously carried out in a temperature range of from about −20° C. to about +150° C., preferably from about −10° C. to about +80° C, particularly preferably from about 0° C. to about +40° C.

In a preferred embodiment, a compound of the formula II is reacted at from 0° C. to 120° C., preferably at 20° C., in a halogenated hydrocarbon, preferably dichloromethane, with a compound of the formula III.

The compounds I can be present in the form of one of the possible isomers or as a mixture thereof, for example, depending on the number and the absolute and relative configuration of the asymmetrically substituted carbon atoms, as pure isomers, such as enantiomers and/or diastereomers, or as isomer mixtures, such as enantiomer mixtures, for example racemates, or diastereomer mixtures or racemate mixtures; the invention relates both to the pure isomers and to all possible isomer mixtures and is to be understood hereinabove and hereinbelow in each case in this sense even when stereochemical details are not mentioned specifically in each case.

Diastereomer mixtures and racemate mixtures of compounds I which can be obtained in accordance with the process—depending on the choice of starting materials and procedures—or by other means can be resolved into the pure diastereomers or racemates in the known manner on the basis of the physico-chemical differences of the components, for example by fractional crystallization, distillation and/or chromatography.

Enantiomer mixtures which can be obtained accordingly, such as racemates, can be separated into the optical antipodes by customary methods, for example by recrystallizabon from an optically active solvent, by chromatography on chiral adsorbents, for example high-performance liquid chromatography (HPLC) on acetylcellulose, with the aid of suitable microorganisms, by cleavage with specific immobilized enzymes, via the formation of inclusion compounds, for example using chiral crown ethers, where only one enantiomer is complexed.

In addition to separating appropriate isomer mixtures, pure diastereomers or enantiomers can also be obtained in accordance with the invention by generally known methods of diastereoselective or enantioselective synthesis, for example by carrying out the process according to the invention with starting materials of a suitable stereochemistry.

It is advantageous to isolate, or synthesize, in each case the biologically more active isomer, for example enantiomer, or isomer mixture, for example enantiomer mixture, if the individual components have different biological activity.

Starting materials and intermediates which are preferably used in the process of the present invention are those which lead to compounds I which have been described at the outset as being particularly useful.

The invention relates in particular to the preparation process described in the example.

The invention also relates to novel starting materials and intermediates used in the preparation of the compounds I, and to their use and to processes for their preparation.

The compounds I according to the invention have a particularly broad activity spectrum and are active compounds which are useful in pest control, in particular in the control of endo- and ectoparasites on animals, while having favourable homeotherm, fish and plant compatibility.

In the context of the present invention, ectoparasites are to be understood as meaning, in particular, insects, mites and ticks. This includes insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, particular mention may be made of ectoparasites which are a nuisance to man or animals and transmit pathogens, such as, for example, flies, such as *Musca domestica, Musca vetustissima, Musca autumnalis, Fannia canicularis, Sarcophaga camaria, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Stomoxys calcitrans, Haematobia irritans* and mosquitoes (Nematocera), such as Culicidae, Simuliidae, Psychodidae, but also blood-sucking parasites, for example fleas, such as *Ctenocephalides felis* and *Ctenocephalides canis* (cat and dog fleas), *Xenopsylla cheopis, Pulex irritans, Dermatophilus penetrans,* lice, such as *Damalina ovis, Pediculus humanis,* biting flies and horse flies (Tabanidae), Haematopota spp., such as *Haematopota pluvialis,* Tabanidea spp., such as *Tabanus nigrovittatus,* Chrysopsinae spp., such as *Chrysops caecutiens,* tsetse flies, such as Glossiniar species, biting insects, in particular cockroaches, such as *Blatella gennanica, Blatta orientalis, Periplaneta americana,* mites, such as *Dermanyssus gallinae, Sarcoptes scabiei, Psoroptes ovis* and Psorergates spp., and last but not least ticks. The latter belong to the order Acarina. Known tick representatives are, for example, Boophilus, Amblyomma, Anocentor, Dermacentor, Haemaphysalis, Hyalomma, Ixodes, Rhipicentor, Margaropus, Rhipicephalus, Argas, Otobius and Ornithodoros and the like which preferably attack warm-blooded animals, including farm animals, such as cows, pigs, sheep and goats, poultry, such as chicken, turkeys and geese, fur-bearing animals, such as mink, foxes, chinchillas, rabbits and the like, and pets, such as cats and dogs, but also humans.

The compounds I can also be used against hygiene pests, in particular of the order Diptera with the families Sarcophagidae, Anophilidae and Culicidae; the orders Orthoptera, Dictyoptera (for example the family Blattidae) and Hymenoptera (for example the family Formicidae).

The compounds I also have lasting activity against phytoparasitic mites and insects. In the case of spider mites of the order Acarina, they are active against eggs, nymphs and adults of Tetranychidae (Tetranychus spp. and Panonychus spp.).

They are highly active against the sucking insects of the order Homoptera, in particular against pests of the families Aphididae, Delphacidae, Cicadellidae, Psyllidae, Loccidae, Diaspididae and Eriophydidae (for example rust mites on citrus fruits); of the orders Hemiptera, Heteroptera and Thysanoptera, and, in the case of plant-feeding insects, of the orders Lepidoptera, Coleoptera, Diptera and Orthoptera.

They are also suitable for use as soil insecticides against pests in the soil.

Accordingly, the compounds of the formula I are active against all development stages of sucking and feeding insects on crops such as cereals, cotton, rice, maize, soya beans, potatoes, vegetables, fruits, tobacco, hops, citrus fruits, avocados and others.

The compounds of the formula I are also active against plant nematodes of the species Meloidogyne, Heterodera, Pratylenchus, Ditylenchus, Radopholus, Rizoglyphus and others.

The compounds are particularly active against helminths, of which the endoparasitic nematodes can be the cause of serious diseases in mammals and poultry, for example in sheep, pigs, goats, cattle, horses, donkeys, dogs, cats, guinea pigs and ornamental birds. Typical nematodes of this indication are: Haemonchus, Trichostrongylus, Ostertagia, Nematodirus, Cooperia, Ascaris, Bunostonum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of the formula I is their activity against parasites which are resistant against active compounds based on benzimidazole.

Certain Nematodirus, Cooperia and Oesophagostonum species attack the intestinal tract of the host animal, whereas others, of the species Haemonchus and Ostertagia and the species Dictyocaulus parasitise in the stomach and in lung tissue, respectively. Parasites of the families Filariidae and Setariidae are found in internal cell tissue and in organs, for example the heart, blood vessels, lymph vessels and subcutaneous tissues. Particular mention may be made here of the heart worm of dogs, Dirofilaria immitis. The compounds of the formula I are highly effective against these parasites.

The compounds of the formula I are, in particular, also suitable for controlling parasites which are pathogenic in humans, typical representatives of which, encountered in the digestive tract, being those of the species Ancylostoma, Necator, Ascaris, Strongyloides, Trichinella, Capillaria, Trichuris and Enterobius. The compounds of the present invention are also active against parasites of the species Wuchereria, Brugia, Onchocerca and Loa from the family of the Filariidae, which are encountered in blood, in tissue and in various organs, and furthermore against Dracunculus and parasites of the species Strongyloides and Trichinella, which infect specifically the gastrointestinal tract.

The good pesticidal action of the compounds of the formula I according to the invention corresponds to a kill rate (mortality) of at least 50–60% among the pests mentioned. In particular, the compounds of the formula I have an extraordinarily long persistency.

The action of the compounds according to the invention and the compositions comprising them against animal pests can be extended substantially and adapted to given circumstances by adding other insecticides and/or acaricides. Suitable additives are, for example, representatives of the following classes of active compounds: organic phosphorus compounds, nitrophenols and derivatives, formamidines, ureas, carbamates, pyrethroids, chlorinated hydrocarbons, neonicotinoids and Bacillus thuringiensis preparations.

The compounds of the formula I are used as such or preferably together with the auxiliaries which are customary in the art of formulation, and they can therefore be processed in a known manner, for example, to emulsifiable concentrates, directly sprayable or dilutable solutions, dilute emulsions, wettable powders, soluble powders, dusts, granules and also encapsulations in polymeric substances. The application methods, such as spraying, atomizing, dusting, broadcasting or watering, like the compositions, are selected so that they are appropriate for the intended aims and the given conditions.

The formulation, i.e. the agents, preparations or compositions comprising the active compound of the formula I, or combinations of these active compounds with other agrochemically active compounds and, if appropriate, a solid or liquid additive, are prepared in a known manner, for example by mixing and/or grinding the active compounds intimately with extenders, for example with solvents, solid carriers and, if appropriate, surfactants.

Suitable solvents are: aromatic hydrocarbons, preferably the fractions $C_8$ to $C_{12}$ of alkylbenzenes, such as xylene mixtures or alkylated naphthalenes, aliphatic or cycloaliphatic hydrocarbons, such as cyclohexane, paraffins or tetrahydronaphthalene, alcohols, such as ethanol, propanol or butanol, and glycols and their ethers and esters, such as propylene glycol, dipropylene glycol ether, ethylene glycol, ethylene glycol monomethyl ether or ethylene glycol monoethyl ether, ketones, such as cyclohexanone, isophorone or diacetone alcohol, strongly polar solvents, such as N-methyl-2-pyrrolidone, dimethyl sulphoxide or dimethylformamide, or water, vegetable oils, such as rapeseed, castor, coconut or soya oil; if appropriate also silicone oils.

The solid carriers used, for example for dusts and dispersible powders, are generally ground natural minerals, such as calcite, talc, kaolin, montmorillonite or attapulgite. To improve the physical properties, it is also possible to add finely divided silicas or finely divided absorptive polymers. Suitable particulate adsorptive carriers for granules are porous types, such as pummice, brick grit, sepiolite or bentonite, and suitable non-sorptive carrier materials are calcite or sand. In addition, a large number of granulated materials of inorganic or organic nature can be used, such as, in particular, dolomite or comminuted plant residues.

Suitable surfactants are, depending on the type of active compound of the formula I or the combinations of these active compounds with other insecticides or acaricides to be formulated, nonionic, cabonic and/or anionic surfactants having good emulsifying, dispersing and wetting properties. Surfactants also include surfactant mixtures.

Suitable anionic surfactants can be both so-called water-soluble soaps and water-soluble synthetic surfactants.

Suitable soaps are the alkali metal, alkaline earth metal or unsubstituted or substituted ammonium salts of higher fatty acids ($C_{10}$–$C_{22}$), such as the sodium or potassium salts of oleic or stearic acid, or of natural fatty acid mixtures which can be obtained, for example, from coconut or tallow oil. Furthermore, mention must also be made, as surfactants, of the fatty acid methyl taurates.

However, so-called synthetic surfactants are used more frequently, in particular fatty sulphonates, fatty sulphates, sulphonated benzimidazole derivatives or alkylaryl sulphonates.

The fatty sulphonates or fatty sulphates are generally present as alkali metal, alkaline earth metal or unsubstituted or substituted ammonium salts and they generally have an alkyl radical of 8 to 22 C atoms, alkyl also being understood as including the alkyl moiety of acyl radicals, for example the sodium or calcium salt of lignosulphonic acid, of the dodecylsulphuric ester or of a fatty alcohol sulphate mixture prepared from natural fatty acids. This group also includes the salts of sulphuric esters and sulphonic acids of fatty alcohol/ethylene oxide adducts. The sulphonated benzimidazole derivatives preferably contain 2 sulphonyl groups and a fatty acid radical of approximately 8–22 C atoms. Examples of alkylaryl sulphonates are the sodium, calcium or triethanolamine salts of dodecylbenzenesulphonic acid, of dibutylnaphthalenesulphonic acid or of a naphthalenesulphonic acid/formaldehyde condensate. Also possible are, furthermore, suitable phosphates, such as salts of the phosphoric ester of a p-nonylphenol/(4–14)ethylene oxide adduct, or phospholipids.

Suitable nonionic surfactants are primarily polyglycol ether derivatives of aliphatic or cycloaliphatic alcohols, saturated or unsaturated fatty acids and alkyl phenols which may contain 3 to 30 glycol ether groups and 8 to 20 carbon atoms in the (aliphatic) hydrocarbon radical and 6 to 18 carbon atoms in the alkyl radical of the alkyl phenols. Other suitable nonionic surfactants are the water-soluble polyethylene oxide adducts to polypropylene glycol, ethylene diaminopolypropylene glycol and alkyl polypropylene glycol having 1 to 10 carbon atoms in the alkyl chain, which contain 2 to 250 ethylene glycol ether groups and 10 to 100 propylene glycol ether groups. The products mentioned usually contain 1 to 5 ethylene glycol units per propylene glycol unit.

Examples of nonionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Also suitable are fatty acid esters of polyoxyethylene sorbitan, such as polyoxyethylene sorbitan trioleate.

The cationic surfactants are, especially, quaternary ammonium salts which have at least one alkyl radical having 8 to 22 C atoms as N-substituent and, as further substituents, lower, unhalogenated or halogenated alkyl, benzyl or lower hydroxy alkyl radicals. The salts are preferably present as halides, methyl sulphates or ethyl sulphates, for example stearyltrimethylammonium chloride or benzyldi(2-chloroethyl)ethylammonium bromide.

The surfactants which are customarily used in the art of formulation are described, for example, in the following publications:

"McCutcheon's Detergents and Emulsifiers Annual", McPublishing Corp., Glen Rock, N.J., USA, 1988", H. Stache, "Tensid-Taschenbuch", 2nd Ed., C. Hanser Verlag Munich, Vienna 1981.

M. and J. Ash. "Encyclopedia of Surfactants", Vol. I–III, Chemical Publishing Co., New York, 1980–1981.

Preferred application forms for use in homeotherms for controlling helminths include solutions, emulsions, suspensions (drenches), feed additives, powders, tablets including effervescent tablets, boluses, capsules, microencapsulations and pour-on formulations, where the formulation auxiliaries have to be physiologically acceptable.

Binders suitable for tablets and boluses are chemically modified water- or alcohol-soluble polymeric natural products such as derivatives of starch, cellulose or protein (for example methylcellulose, carboxymethylcellulose, ethylhydroxyethylcellulose, proteins such as zein, gelatin and the like) and synthetic polymers, for example polyvinyl alcohol, polyvinylpyrrolidone etc. Tablets also contain fillers (for example starch, microcrystalline cellulose, sugar, lactose, etc.), lubricants and disintegrants.

If the anthelmintic compositions are present in the form of feed concentrates, the carriers are, for example, high-performance feed, feed cereals or protein concentrates. Such feed concentrates or compositions may, in addition to the active compounds, also comprise additives, vitamins, antibiotics, chemotherapeutics, or other pesticides, mainly bacteriostatics, fungistatics, coccidiostatics, or else hormone preparations, anabolics or substances which promote growth, improve the meat quality of animals for slaughter or benefit the organism in another way. If the compositions or the active compounds of the formula I contained therein are added directly to the feed or to the drinking water for the animals, the finished feed or the finished drinking water preferably contains the active compounds in a concentration of approximately 0.0005 to 0.02% by weight (5–200 ppm).

The compositions according to the invention can be administered topically, perorally, parenterally or subcutaneously to the animals to be treated, the compositions being present in the form of solutions, emulsions, suspensions (drenches), powders, tablets, boluses, capsules or as pour-on formulations.

The compounds of formula I according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. If the range of activity is to be extended to endoparasites, e.g. wormers, the compounds of formula I are suitably combined with substances having endoparasitic properties. Of course, they can also be used in combination with antibacterial compositions. Since the compounds of formula I are adulticides, i.e. since they are effective in particular against the adult stage of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula I.

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers.

Non-limitative examples of suitable insecticides and acaricides are:

| | |
|---|---|
| 1. Abamectin | 97. Hexythiazox |
| 2. AC 303 630 | 98. Hydroprene |
| 3. Acephat | 99. Imidacloprid |
| 4. Acrinathrin | 100. insect-active fungi |
| 5. Alanycarb | 101. insect-active nematodes |
| 6. Aldicarb | |
| 7. Alpha-Cypermethrin | 102. insect-active viruses |
| 8. Alphamethrin | 103. Iprobenfos |
| 9. Amitraz | 104. Isofenphos |
| 10. Avermectin B$_1$ | 105. Isoprocarb |
| 11. AZ 60541 | 106. Isoxathion |
| 12. Azinphos A | 107. Ivermectin |
| 13. Azinphos M | 108. Lambda-Cyhalothrin |
| 14. Azinphos-methyl | 109. Lambda-cyhalothrin |
| 15. Azocyclotin | 110. Lufenuron |
| 16. *Bacillus subtilis* toxin | 111. Malathion |
| 17. Bendiocarb | 112. Mecarbam |
| 18. Benfuracarb | 113. Mesulfenphos |
| 19. Bensultap | 114. Metaldehyd |
| 20. Betacyfluthrin | 115. Methamidophos |
| 21. beta-Cyfluthrin | 116. Methiocarb |
| 22. Bifenthrin | 117. Methomyl |
| 23. BPMC | 118. Methoprene |
| 24. Brofenprox | 119. Metolcarb |
| 25. Bromophos A | 120. Mevinphos |
| 26. Bufencarb | 121. Milbemectin |
| 27. Buprofezin | 122. Moxidectin |
| 28. Butocarboxin | 123. Naled |
| 29. Butylpyridaben | 124. NC 184 |
| 30. Cadusafos | 125. NI-25, Acetamiprid |
| 31. Carbaryl | 126. Nitenpyram |
| 32. Carbofuran | 127. Omethoat |

-continued

| | |
|---|---|
| 33. Carbophenthion | 128. Oxamyl |
| 34. Cartap | 129. Oxydemethon M |
| 35. Chloethocarb | 130. Oxydeprofos |
| 36. Chlorethoxyfos | 131. Parathion |
| 37. Chlorfenapyr | 132. Parathionmethyl |
| 38. Chlorfluazuron | 133. Permethrin |
| 39. Chlormephos | 134. Phenthoat |
| 40. Chlorpyrifos | 135. Phorat |
| 41. Cis-Resmethrin | 136. Phosalone |
| 42. Clocythrin | 137. Phosmet |
| 43. Clofentezin | 138. Phoxim |
| 44. Cyanophos | 139. Pirimicarb |
| 45. Cycloprothrin | 140. Pirimiphos A |
| 46. Cyfluthrin | 141. Pirimiphos M |
| 47. Cyhexatin | 142. Promecarb |
| 48. D 2341 | 143. Propaphos |
| 49. Deltamethrin | 144. Propoxur |
| 50. Demeton M | 145. Prothiofos |
| 51. Demeton S | 146. Prothoat |
| 52. Demeton-S-methyl | 147. Pyrachlophos |
| 53. Dibutylaminothio | 148. Pyradaphenthion |
| 54. Dichlofenthion | 149. Pyresmethrin |
| 55. Dicliphos | 150. Pyrethrum |
| 56. Diethion | 151. Pyridaben |
| 57. Diflubenzuron | 152. Pyrimidifen |
| 58. Dimethoat | 153. Pyriproxyfen |
| 59. Dimethylvinphos | 154. RH 5992 |
| 60. Dioxathion | 155. RH-2485 |
| 61. DPX-MP062 | 156. Salithion |
| 62. Edifenphos | 157. Sebufos |
| 63. Emamectin | 158. Silafluofen |
| 64. Endosulfan | 159. Spinosad |
| 65. Esfenvalerat | 160. Sultotep |
| 66. Ethiofencarb | 161. Sulprofos |
| 67. Ethion | 162. Tebufenozide |
| 68. Ethofenprox | 163. Tebufenpyrad |
| 69. Ethoprophos | 164. Tebupirimphos |
| 70. Etrimphos | 165. Teflubenzuron |
| 71. Fenamiphos | 166. Tefluthrin |
| 72. Fenazaquin | 167. Temephos |
| 73. Fenbutatinoxid | 168. Terbam |
| 74. Fenitrothion | 169. Terbufos |
| 75. Fenobucarb | 170. Tetrachlor-vinphos |
| 76. Fenothiocarb | 171. Thiafenox |
| 77. Fenoxycarb | 172. Thiodicarb |
| 78. Fenpropathrin | 173. Thiofanox |
| 79. Fenpyrad | 174. Thionazin |
| 80. Fenpyroximate | 175. Thuringiensin |
| 81. Fenthion | 176. Tralomethrin |
| 82. Fenvalerate | 177. Triarthen |
| 83. Fipronil | 178. Triazamate |
| 84. Fluazinam | 179. Triazophos |
| 85. Fluazuron | 180. Triazuron |
| 86. Flucycloxuron | 181. Trichlorfon |
| 87. Flucythrinat | 182. Triflumuron |
| 88. Flufenoxuron | 183. Trimethacarb |
| 89. Flufenprox | 184. Vamidothion |
| 90. Fonophos | 185. XMC (3,5,-Xylyl methylcarbamat) |
| 91. Formothion | 186. Xylylcarb |
| 92. Fosthiazat | 187. YI 5301/5302 |
| 93. Fubfenprox | 188. zeta-Cypermethrin |
| 94. HCH | 189. Zetamethrin |
| 95. Heptenophos | |
| 96. Hexaflumuron | |

Non-limitative examples of suitable anthelminthics are named in the following, a few representatives have insecticidal and acaricidal activity in addition to the anthelminthic activity, and are partly already in the above list.

(A1) Praziquantel=2-cyclohexylcarbonyl-4-oxo-1,2,3,6,7,11b-hexahydro-4H-pyrazino[2,1-α]isoquinoline
(A2) Closantel=3,5-diiodo-N-[5-chloro-2-methyl-4-(a-cyano-4-chlorobenzyl)phenyl]-salicylamide
(A3) Triclabendazole=5-chloro-6-(2,3-dichlorophenoxy)-2-methylthio-1H-benzimidazole
(A4) Levamisol=L-(−)-2,3,5,6-tetrahydro-6-phenylimidazo[2,1b]thiazole
(A5) Mebendazole=(5-benzoyl-1H-benzimidazol-2-yl)carbaminic acid methylester
(A6) OmDhalotin=a macrocyclic fermentation product of the fungus Omphalotus olearius described in WO 97/20857
(A7) Abamectin=avermectin B1
(A8) Ivermectin=22,23-dihydroavermectin B1
(A9) Moxidectin=5-O-demethyl-28-deoxy-25-(1,3-dimethyl-1-butenyl)-6,28-epoxy-23-(methoxyimino)-milbemycin B
(A10) Doramectin=25-cyclohexyl-5-O-demethyl-25-de(1-methylpropyl)-avermectin A1a
(A11) Milbemectin=mixture of milbemycin A3 and milbemycin A4
(A12) Milbemycinoxim=5-oxim of milbemectin Non-limitative examples of suitable repellents and detachers are:
(R1) DEET (N, N-diethyl-m-toluamide)
(R2) KBR 3023 N-butyl-2-oxycarbonyl-(2-hydroxy)-piperidine
(R3) Cymiazole=N,-2,3-dihydro-3-methyl-1,3-thiazol-2-ylidene-2,4-xylidene The said partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature. Therefore, the following listing is restricted to a few places where they may be found by way of example.

(I) 2-Methyl-2-(methylthio)propionaldehyd-O-Methylcarbamoyloxime (Aldicarb), from The Pesticide Manual, 11$^{th}$ Ed. (1997), The British Crop Protection Council, London, page 26;

(II) S(3,4-Dihydro4-oxobenzo[d]-[1,2,3]-triazin-3-ylmethyl)O,O-dimethyl-phosphorodithioate (Azinphos-methyl), from The Pesticide Manual, 11$^{th}$Ed. (1997), The British Crop Protection Council, London, page 67;

(III) Ethyl-N-[2,3-dihydro-2,2-dimethylbenzofuran-7-yloxycarbonyl-(methyl)aminothio]-N-isopropyl-β-alaninate (Benfuracarb), from The Pesticide Manual, 11$^{th}$Ed. (1997), The British Crop Protection Council, London, page 96;

(IV) 2-Methylbiphenyl-3-ylmethyl-(2)-(1RS)-cis-3-(2-chlor-3,3,3-trifluorprop-1-enyl)-2,2-dimethylcyclopropancarboxylate (Bifenthrin), from The Pesticide Manual,1$^{th}$Ed. (1997), The British Crop Protection Council, London, page 118;

(V) 2-tert-Butylimino-3-isopropyl-5-phenyl-1,3,5-thiadiazian-4-one (Buprofezin), from The Pesticide Manual, 11$^{th}$Ed. (1997), The British Crop Protection Council, London, page 157;

(VI) 2,3-Dihydro-2,2-dimethylbenzofuran-7-yl-methylcarbamate (Carbofuran), from The Pesticide Manual, 11$^{th}$Ed. (1997), The British Crop Protection Council, London, page 186;

(VII) 2,3-Dihydro-2,2-dimethylbenzofuran-7-yl-(dibutylaminothio)methylcarbamate (Carbosulfan), from The Pesticide Manual, 11$^{th}$Ed. (1997), The British Crop Protection Council, London, page 188;

(VIII) S,S-(2-Dimethylaminotrimethylene)-bis (thiocarbamate) (Cartap), from The Pesticide Manual, 11$^{th}$Ed. (1997), The British Crop Protection Council, London, page 193;

(IX) 1-[3,5-Dichloro-4-(3-chloro-5-trifluoromethyl-2-pyridyloxy)phenyl]-3-(2,6-difluorobenzoyl)-urea (Chlorfluazuron), from The Pesticide Manual, 11$^{th}$Ed. (1997), The British Crop Protection Council, London, page 213;

(X) O,O-Diethyl-O-3,5,6-trichloro-2-pyridyl-phosphorothioate (Chlorpyrifos), from The Pesticide Manual, 11$^{th}$Ed. (1997), The British Crop Protection Council, London, page 235;

(XI) (RS)-α-Cyano-4-fluoro-3-phenoxybenzyl-(1RS, 3RS;1RS,3RS)-3-(2,2-dichlorovinyl)-2,2-dimethylcyclopropancarboxylate (Cyfluthrin), from The Pesticide Manual, 11$^{th}$Ed. (1997), The British Crop Protection Council, London, page 293;

(XII) Mixture of (S)-α-Cyano-3-phenoxybenzyl-(Z)-(1R,3R)-3-(2-chloro-3,3,3-trifluoropropenyl)-2,2-dimethylcyclopropanecarboxylate and (R)-α-cyano-3-phenoxybenzyl-(Z)-(1R,3R)-3-(2-chloro-3,3,3-trifluoropropenyl)-2,2-dimethylcyclopropanecarboxylate (Lambda-Cyhalothrin), from The Pesticide Manual, 11$^{th}$Ed. (1997), The British Crop Protection Council, London, page 300;

(XIII) Racemate consisting of (S)-α-cyano-3-phenoxybenzyl-(1R,3R)-3-(2,2-dichlorovinyl)-2,2-dimethylcyclopropanecarboxylate and (R)-α-cyano-3-phenoxybenzyl-(1S,3S)-3-(2,2-dichlorovinyl)-2,2-dimethylcyclopropanecarboxylate (Alpha-cypermethrin), from The Pesticide Manual, 11$^{th}$Ed. (1997), The British Crop Protection Council, London, page 308;

(XIV) Mixture of the stereoisomers of (S)-α-cyano-3-phenoxybenzyl (1RS,3RS,1RS,3RS)-3-(2,2-dichlorovinyl)-2,2-dimethylcyclopropanecarboxylate (zeta-Cypermethrin), from The Pesticide Manual,11$^{th}$Ed. (1997), The British Crop Protection Council, London, page 314;

(XV) (S)-α-cyano-3-phenoxybenzyl-(1R,3R)-3-(2,2-dibromovinyl)-2,2-dimethylcyclopropane-carboxylate (Deltamethrin), from The Pesticide Manual, 11$^{th}$Ed. (1997), The British Crop Protection Council, London, page 344;

(XVI) (4-Chlorophenyl)-3-(2,6-difluorobenzoyl)urea (Diflubenzuron), from The Pesticide Manual, 11$^{th}$Ed. (1997), The British Crop Protection Council, London, page 395;

(XVII) (1,4,5,6,7,7-Hexachloro-8,9,10-trinorborn-5-en-2,3-ylenbismethylene)-sulphite (Endosulfan), from The Pesticide Manual, 11$^{th}$Ed. (1997), The British Crop Protection Council, London, page 459;

(XVIII) α-Ethylthio-o-tolyl-methylcarbamate (Ethiofencarb), from The Pesticide Manual, 11$^{th}$Ed. (1997), The British Crop Protection Council, London, page 479;

(XIX) O,O-Dimethyl-O-4-nitro-m-tolyl-phosphorothioate (Fenitrothion), from The Pesticide Manual, 11$^{th}$Ed. (1997), The British Crop Protection Council, London, page 514;

(XX) 2-sec-Butylphenyl-methylcarbamate (Fenobucarb), from The Pesticide Manual, 11$^{th}$Ed. (1997), The British Crop Protection Council, London, page 516;

(XXI) (RS)-α-Cyano-3-phenoxybenzyl-(RS)-2-(4-chlorophenyl)-3-methylbutyrate (Fenvalerate), from The Pesticide Manual, 11$^{th}$Ed. (1997), The British Crop Protection Council, London, page 539;

(XXII) S[Formyl(methyl)carbamoylmethyl]-O,O-dimethyl-phosphorodithioate (Formothion), from The Pesticide Manual, 11$^{th}$ed. (1997), The British Crop Protection Council, London, page 625;

(XXIII) 4-Methylthio-3,5-xylyl-methylcarbamate (Methiocarb), from The Pesticide Manual, 11$^{th}$Ed. (1997), The British Crop Protection Council, London, page 813;

(XXIV) 7-Chlorbicyclo[3.2.0]hepta-2,6-dien-6-yldimethylphosphate (Heptenophos), from The Pesticide Manual, 11$^{th}$Ed. (1997), The British Crop Protection Council, London, page 670;

(XXV) 1-(6-Chloro-3-pyridylmethyl)-N-nitroimidazolidin-2-ylidenamine (Imidacloprid), from The Pesticide Manual, 11$^{th}$Ed. (1997), The British Crop Protection Council, London, page 706;

(XXVI) 2-Isopropylphenyl-methylcarbamate (Isoprocarb), from The Pesticide Manual, 11$^{th}$Ed. (1997), The British Crop Protection Council, London, page 729;

(XXVII) O,S-Dimethyl-phosphoramidothioate (Methamidophos), from The Pesticide Manual, 11$^{th}$Ed. (1997), The British Crop Protection Council, London, page 808;

(XXVIII) S-Methyl-N-(methylcarbamoyloxy) thioacetimidate (Methomyl), from The Pesticide Manual, 11$^{th}$Ed. (1997), The British Crop Protection Council, London, page 815;

(XXIX) Methyl-3-(dimethoxyphosphinoyloxy)but-2-enoate (Mevinphos), from The Pesticide Manual, 11$^{th}$Ed. (1997), The British Crop Protection Council, London, page 844;

(XXX) O,O-Diethyl-O-4-nitrophenyl-phosphorothioate (Parathion), from The Pesticide Manual, 11$^{th}$Ed. (1997), The British Crop Protection Council, London, page 926;

(XXXI) O,O-Dimethyl-O-4-nitrophenyl-phosphorothioate (Parathion-methyl), from The Pesticide Manual, 11$^{th}$Ed. (1997), The British Crop Protection Council, London, page 928;

(XXXII) S-6-Chloro-2,3-dihydro-2-oxo-1,3-benzoxazol-3-ylmethyl-O,O-diethyl-phosphordithioate (Phosalone), from The Pesticide Manual, 11$^{th}$Ed. (1997), The British Crop Protection Council, London, page 963;

(XXXIII) 2-Dimethylamino-5,6-dimethylpyrimidin-4-yl-dimethylcarbamate (Pirimicarb), from The Pesticide Manual, 11$^{th}$Ed. (1997), The British Crop Protection Council, London, page 985;

(XXXIV) 2-Isopropoxyphenyl-methylcarbamate (Propoxur), from The Pesticide Manual, 11$^{th}$Ed. (1997), The British Crop Protection Council, London, page 1036;

(XXXV) 1-(3,5-Dichloro-2,4-difluorophenyl)-3-(2,6-difluorobenzoyl)urea (Teflubenzuron), from The Pesticide Manual, 11$^{th}$Ed. (1997), The British Crop Protection Council, London, page 1158;

(XXXVI) S-tert-butylthiomethyl-O,O-dimethyl-phosphorodithioate (Terbufos), from The Pesticide Manual, 11$^{th}$Ed. (1997), The British Crop Protection Council, London, page 1165;

(XXXVII) Ethyl-(3-tert.-butyl-1-dimethylcarbamoyl-1H-1,2,4-triazol-5-yl-thio)-acetate, (Triazamate), from The Pesticide Manual, 11$^{th}$Ed. (1997), The British Crop Protection Council, London, page 1224;

(XXXVIII) Abamectin, from The Pesticide Manual, 11$^{th}$Ed. (1997), The British Crop Protection Council, London, page 3;

(XXXIX) 2-sec-butylphenyl-methylcarbamate (Fenobucarb), from The Pesticide Manual, 11$^{th}$Ed. (1997), The British Crop Protection Council, London, page 516;

(XL) N-tert.-butyl-N-(4-ethylbenzoyl)-3,5-dimethylbenzohydrazide (Tebufenozide), from The Pesticide Manual, 11$^{th}$Ed. (1997), The British Crop Protection Council, London, page 1147;

(XLI) (±)-5-Amino-1-(2,6-dichloro-α,α,α-trifluoro-p-tolyl) 4-trifluoromethyl-sulphinylpyrazol-3-carbonitrile (Fipronil), from The Pesticide Manual, 11$^{th}$Ed. (1997), The British Crop Protection Council, London, page 545;

(XLII) (RS)-α-cyano-4-fluoro-3-phenoxybenzyl(1RS, 3RS;1RS,3RS)-3-(2,2-dichlorovinyl)-2,2- dimethylcyclopropanecarboxylate (beta-Cyfluthrin), from The Pesticide Manual, 11$^{th}$Ed. (1997), The British Crop Protection Council, London, page 295;

(XLIII) (4-Ethoxyphenyl)-[3-(4-fluoro-3-phenoxyphenyl) propyl](dimethyl)silane (Silafluofen), from The Pesticide Manual, 11$^{th}$Ed. (1997), The British Crop Protection Council, London, page 1105;

(XLIV) tert.-butyl(E)-α-(1,3-dimethyl-5-phenoxypyrazol-4-yl-methylenamino-oxy)-p-toluate (Fenpyroximate), from The Pesticide Manual, 11$^{th}$Ed. (1997), The British Crop Protection Council, London, page 530;

(XLV) 2-tert.-butyl-5-(4-tert.-butylbenzylthio)-4-chloropyridazin-3(2H-one (Pyridaben), from The Pesticide Manual, 11$^{th}$Ed. (1997), The British Crop Protection Council, London, page 1161;

(XLVI) 4-[[4-(1,1-dimethylphenyl)phenyl]ethoxy]-quinazoline (Fenazaquin), from The Pesticide Manual, 11$^{th}$Ed. (1997), The British Crop Protection Council, London, page 507;

(XLVII) 4-Phenoxyphenyl-(RS)-2-(pyridyloxy)propyl-ether (Pyriproxyfen), from The Pesticide Manual, 11$^{th}$Ed. (1997), The British Crop Protection Council, London, page 1073;

(XLVIII) 5-Chloro-N-{2-[4-(2-ethoxyethyl)-2,3-dimethylphenoxy]ethyl}-6-ethylpyrimidin-4-amine (Pyrimidifen), from The Pesticide Manual, 11$^{th}$Ed. (1997), The British Crop Protection Council, London, page 1070;

(XLIX) (E)-N-(6-chloro-3-pyridylmethyl)-N-ethyl-N-methyl-2-nitrovinylidenediamine (Nitenpyram), from The Pesticide Manual, 11$^{th}$Ed. (1997), The British Crop Protection Council, London, page 880;

(L) (E)-N$^1$-[(6-chloro-3-pyridyl)methyl]-N$^2$-cyano-N$^1$-methylacetamidine (NI-25, Acetamiprid), from The Pesticide Manual, 11$^{th}$Ed. (1997), The British Crop Protection Council, London, page 9;

(LI) Avermectin B$_1$, from The Pesticide Manual, 11$^{th}$Ed. (1997), The British Crop Protection Council, London, page 3;

(LII) an insect-active extract from a plant, especially (2R, 6aS,12aS)-1,2,6,6a,12,12a-hexhydro-2-isopropenyl-8,9-dimethoxy-chromeno[3,4-b]furo[2,3-h]chromen-6-one (Rotenone), from The Pesticide Manual, 11$^{th}$Ed. (1997), The British Crop Protection Council, London, page 1097; and an extract from *Azadirachta indica*, especially azadirachtin, from The Pesticide Manual, 11$^{th}$Ed. (1997), The British Crop Protection Council, London, page 59; and (LIII) a preparation which contains insect-active nematodes, preferably *Heterorhabditis bacteriophora* and *Heterorhabditis megidis*, from The Pesticide Manual, 11$^{th}$Ed. (1997), The British Crop Protection Council, London, page 671; *Steinemema feltiae*, from The Pesticide Manual, 11$^{th}$Ed. (1997), The British Crop Protection Council, London, page 1115 and *Steinemema scapterisci*, from The Pesticide Manual, 11$^{th}$Ed. (1997), The British Crop Protection Council, London, page 1116;

(LIV) a preparation obtainable from *Bacillus subtilis*, from The Pesticide Manual, 11$^{th}$Ed. (1997), The British Crop Protection Council, London, page 72; or from a strain of *Bacillus thuringiensis* with the exception of compounds isolated from GC91 or from NCTC11821; The Pesticide Manual, 11$^{th}$Ed. (1997), The British Crop Protection Council, London, page 73;

(LV) a preparation which contains insect-active fungi, preferably *Verticillium lecanii*, from The Pesticide Manual, 11$^{th}$Ed. (1997), The British Crop Protection Council, London, page 1266; *Beauveria brogniartii*, from The Pesticide Manual, 11$^{th}$Ed. (1997), The British Crop Protection Council, London, page 85 and *Beauveria bassiana*, from The Pesticide Manual, 11$^{th}$Ed. (1997), The British Crop Protection Council, London, page 83;

(LVI) a preparation which contains insect-active viruses, preferably Neodipridon Sertifer NPV, from The Pesticide Manual, 11$^{th}$Ed. (1997), The British Crop Protection Council, London, page 1342; *Mamestra brassicae* NPV, from The Pesticide Manual, 11$^{th}$Ed. (1997), The British Crop Protection Council, London, page 759 and *Cydia pomonella granulosis* virus, from The Pesticide Manual, 11$^{th}$Ed. (1997), The British Crop Protection Council, London, page 291;

(CLXXXI) 7-Chloro-2,3,4a,5-tetrahydro-2-[methoxycarbonyl(4-trifluoromethoxyphenyl)-carbamoyl]indole[1,2e]oxazolin-4a-carboxylat e(DPX-MP062, Indoxycarb), from The Pesticide Manual, 11$^{th}$Ed. (1997), The British Crop Protection Council, London, page 453;

(CLXXXII) N'-tert.-butyl-N'-(3,5-dimethylbenzoyl)-3-methoxy-2-methylbenzohydrazide (RH-2485, Methoxytenozide), from The Pesticide Manual, 11$^{th}$Ed. (1997), The British Crop Protection Council, London, page 1094; and (CLXXXIII) (N'-[4-methoxy-biphenyl-3-yl]-hydrazinecarboxylic acid isopropyl ester (D 2341), from Brighton Crop Protection Conference, 1996, 487–493;

(R2) Book of Abstracts, 212th ACS National Meeting Orlando, Fla., Aug. 25–29 (1996), AGRO-020. Publisher: American Chemical Society, Washington, D.C. CONEN: 63BFAF.

As a consequence of the above details, a further essential aspect of the present invention relates to combination preparations for the control of parasites on warm-blooded animals, characterised in that they contain, in addition to a compound of formula I, at least one further active ingredient having the same or different sphere of activity and at least one physiologically acceptable carrier. The present invention is not restricted to two-fold combinations.

The anthelmintic compositions according to the invention generally comprise 0.1 to 99% by weight, in particular 0.1 to 95% by weight, of active compound of the formula I, Ia or mixtures thereof, 99.9 to 1% by weight, in particular 99.8 to 5% by weight, of a solid or liquid additive, including 0 to 25% by weight, in particular 0.1 to 25% by weight, of a surfactant.

The pour-on or spot-on method comprises applying the compound of the formula I to a locally restricted area of skin or hide, preferably on the neck or back of the animal. This is carried out, for example, by applying a drop or squirt of the pour-on or spot-on formulation to a relatively small area of the hide, from which the active substance is spread virtually unaided over wide regions of the hide, owing to the spreading components of the formulation and supported by the movements of the animal.

Pour-on and spot-on formulations advantageously comprise carriers which promote rapid distribution on the surface of the skin or the hide of the host animal and are generally referred to as spreading oils. Suitable are, for example oily solutions; alcoholic and isopropanolic solutions, for example solutions of 2-octyldodecanol or oleyl alcohol; solutions in esters of monocarboxylic acids, such as isopropyl myristate, isopropyl palmitate, oxalyl laurinate, oleyl oleate, decyl oleate, hexyl laurate, capric acid esters of saturated fatty alcohols of chain length $C_{12}$–$C_{18}$; solutions of esters of dicarboxylic acids, such as dibutyl phthalate, diisopropyl isophthalate, diisopropyl adipate, di-n-butyl adipate or else solutions of esters of aliphatic acids, for example glycols. The additional presence of a dispersant known from the pharmaceutical or cosmetic industry may be advantageous. Examples are 2-pyrrolidone, 2-(N-alkyl)pyrrolidone, acetone, polyethylene glycol and ethers and esters thereof, propylene glycol or synthetic triglycerides.

The oily solutions include, for example, vegetable oils, such as olive oil, peanut oil, sesame oil, pine oil, linseed oil or castor oil. The vegetable oils can also be present in epoxidized form. It is also possible to use paraffins and silicone oils.

In general, a pour-on or spot-on formulation comprises 1 to 20% by weight of a compound of the formula I, 0.1 to 50% by weight of dispersant and 45 to 98.9% by weight of solvent.

The pour-on or spot-on method can be employed particularly advantageously with gregaripus animals, such as cattle, horses, sheep or pigs, where oral treatment of all the animals or treatment by injection would be difficult or time-consuming. Owing to its simplicity, this method can, of course, also be employed for all other animals, including individual domestic animals or pets, and is very popular with pet owners, because it is frequently possible to carry out this method without the expert help of a veterinarian.

While concentrated compositions are more preferred as commercially available goods, the end user generally uses dilute compositions.

Such compositions may comprise further additives, such as stabilizers, antifoams, viscosity regulators, binders, tackifiers and other active compounds to obtain specific effects.

Such anthelmintic compositions used by the end user also form part of the subject-matter of the present invention.

In each of the methods according to the invention for controlling pests or the pesticides according to the invention, the active compounds of the formula I can be employed in all their steric configurations or mixtures thereof.

The invention also includes a method for prophylactic protection of homeotherms, in particular of useful animals, domestic animals and pets, against parasitic helminths, which comprises applying the active compounds of the formula I or the active compound formulations prepared therefrom as a feed or drinking water additive or else in solid or liquid form, orally, by injection or parenterally, to the animals. The invention also includes the compounds of the formula I according to the invention for use in one of the methods mentioned.

The examples below only serve to illustrate the invention, without limiting it, the term "active compound" representing one of the substances listed in Table 1.

Preferred formulations are, in particular, of the following composition:

(%=per cent by weight)

Formulation Examples

| 1. Emulsion concentrates | a) | b) | c) |
|---|---|---|---|
| Active compound | 25% | 40% | 50% |
| Ca dodecylbenzene sulphonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |

-continued

| 1. Emulsion concentrates | a) | b) | c) |
|---|---|---|---|
| Cyclohexanone | — | 15% | 20% |
| Xylene mixture | 65% | 25% | 20% |

These concentrates can be used to prepare emulsions of any desired concentration, by dilution with water.

| 2. Emulsion concentrates | a) | b) | c) |
|---|---|---|---|
| Active compound | 10% | 8% | 60% |
| Octylphenol polyethylene glycol ether (4–5 mol of ethylene oxide) | 3% | 3% | 2% |
| Ca dodecylbenzene sulphonate | 3% | 4% | 4% |
| Castor oil polyethylene glycol ether (35 mol of ethylene oxide) | 4% | 5% | 4% |
| Cyclohexanone | 30% | 40% | 15% |
| Xylene mixture | 50% | 40% | 15% |

These concentrates can be used to prepare emulsions of any desired concentration, by dilution with water.

| 3. Suspension concentrate | |
|---|---|
| Active compound | 40% |
| Ethylene glycol | 10% |
| Nonylphenol polyethylene glycol ether (15 mol of ethylene oxide) | 6% |
| Na lignosulphonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active compound is mixed intimately with the additives. This gives a suspension concentrate which can be used to prepare suspensions of any desired concentration, by dilution with water.

| 4. Water-dispersible powder mixtures | a) | b) | c) |
|---|---|---|---|
| Active compound | 25% | 50% | 75% |
| Na lignosulphonate | 5% | 5% | — |
| Oleic acid | 3% | — | 5% |
| Na diisobutylnaphthalene sulphonate | — | 6% | 10% |
| Octylphenol polyethylene glycol ether (7–8 mol of ethylene oxide) | — | 2% | — |
| Finely divided silica | 5% | 10% | 10% |
| Kaolin | 62% | 27% | — |

The active compound is mixed intimately with the additives and ground finely in a suitable mill. This gives wettable powders which can be diluted with water to give suspensions of any desired concentration.

| 5. Dusts | a) | b) |
|---|---|---|
| Active compound | 2% | 5% |
| Finely divided silica | 1% | 5% |

-continued

| 5. Dusts | a) | b) |
|---|---|---|
| Talc | 97% | — |
| Kaolin | — | 90% |

Intimate mixing of the carriers with the active compound and grinding of the mixture gives ready-to-use dusts.

| 6. Granules | a) | b) |
|---|---|---|
| Active compound | 5% | 10% |
| Kaolin | 94% | — |
| Finely divided silica | 1% | — |
| Attapulgite | — | 90% |

The active compound is dissolved in methylene chloride and sprayed onto the carrier, and the solvent is then evaporated under reduced pressure. Such granules can be mixed into the animal feed.

| 7. Granules | |
|---|---|
| Active compound | 10% |
| Na lignosulphonate | 2% |
| Carboxymethylcellulose | 1% |
| Kaolin | 87% |

The active compound is mixed with the additives, ground and moistened with water. This mixture is extruded and then dried in a stream of air.

| 8. Granules | |
|---|---|
| Active compound | 3% |
| Polyethylene glycol (MW 200) | 3% |
| Kaolin | 94% |

(MW=molecular weight)

In a mixer, the finely ground active compound is applied evenly to the kaolin, moistened with polyethylene glycol. This gives dust-free coated granules.

9. Tablets or Boluses

| 9. Tablets or Boluses | | | |
|---|---|---|---|
| I | Active compound | 33.00% | |
| | Methylcellulose | 0.80% | |
| | Finely divided silica | 0.80% | |
| | Maize starch | 8.40% | |
| II | cryst. Lactose | 22.50% | |
| | Maize starch | 17.00% | |
| | Microcryst. Cellulose | 16.50% | |
| | Magnesium stearate | 1.00% | |

I Methylcellulose is stirred into water. When the material has swollen, silica is stirred in, and the mixture is suspended homogeneously. Active compound and maize starch are mixed. The aqueous suspension is incorporated into this mixture and kneaded to give a dough. The resulting material is granulated through a 12 M screen and dried.

II All 4 auxiliaries are mixed intimately.

III The premixes obtained according to I and II are mixed and tableted or pressed into boluses.

10. Injectables

A. Oily Vehicle (Slow Release)

| 1. | Active compound | 0.1–1.0 g |
|---|---|---|
| | Peanut oil | approx. 100 ml |
| 2. | Active compound | 0.1–1.0 g |
| | Sesame oil | ad 100 ml |

Preparation: With stirring and, if appropriate, gentle heating, the active compound is dissolved in some of the oil and, after cooling, made up to the intended volume and sterile-filtered through a suitable 0.22 mm membrane filter.

B. Water-miscible Solvent (Medium Release Rate)

| | |
|---|---|
| Active compound | 0.1–1.0 g |
| 4-Hydroxymethyl-1,3-dioxolane (glycerol formal) | 40 g |
| 1,2-Propanediol | ad 100 ml |
| An active compound | 0.1–1.0 g |
| Glycerol dimethyl ketal | 40 g |
| 1,2-Propanediol | ad 100 ml |

Preparation: With stirring, the active compound is dissolved in some of the solvent, made up to the intended volume and sterile-filtered through a suitable 0.22 mm membrane filter.

C. Aqueous Solubilizate (Rapid Release)

| 1. | Active compound | 0.1–1.0 g |
|---|---|---|
| | Polyethoxylated castor oil | 10 g |
| | (40 ethylene oxide units) | |
| | 1,2-Propanediol | 20 g |
| | Benzyl alcohol | 1 g |
| | Water for injection | ad 100 ml |
| 2. | Active compound | 0.1–1.0 g |
| | Polyethoxylated sorbitan monooleate | 8 g |
| | (20 ethylene oxide units) | |
| | 4-Hydroxymethyl-1,3 dioxolane | 20 g |
| | (glycerol formal) | |
| | Benzyl alcohol | 1 g |
| | Water for injection | ad 100 ml |

Preparation: The active compound is dissolved in the solvents and the surfactant and made up to the intended volume with water. Sterile filtration through a suitable membrane filter with a pore diameter of 0.22 mm.

11. Pour-on

| | |
|---|---|
| A. | |
| Active compound | 5 g |
| Isopropyl myristate | 10 g |
| Isopropanol | ad 100 ml |
| B. | |
| Active compound | 2 g |
| Hexyl laurate | 5 g |
| Triglycerides of medium chain length | 15 g |
| Ethanol | ad 100 ml |
| C. | |
| Active compound | 2 g |
| Oleyl oleate | 5 g |

-continued

| | |
|---|---|
| N-Methylpyrrolidone | 40 g |
| Isopropanol | ad 100 ml |

The aqueous systems can preferably also be employed for oral and/or intraruminal administration.

The compositions may also comprise further additives, such as stabilizers, for example epoxidized or non-epoxidized vegetable oils (epoxidized coconut oil, rapeseed oil or soya oil), antifoams, for example silicone oil, preservatives, viscosity regulators, binders, tackifiers and fertilizers or other active compounds to obtain special effects.

Further biologically active substances or additives which are neutral towards the compounds of formula I and have no adverse effect on the host animal to be treated, and mineral salts or vitamins, may also be added to the compositions described above.

The examples below serve to illustrate the invention. They do not limit the invention. The symbol "h" denotes hour.

PREPARATION EXAMPLE
4-Chloro-3-trifluoromethyl-1-methylpyrazole-{N-methyl-N-(3-trichloromethyl-1,2,4-thiadiazol-5-yl)}-carboxamide At room temperature, 140 mg of 4-chloro-1-methyl-3-trifluoropyrazole-5-carboxylic acid are dissolved in 1.55 g of oxalyl chloride, 1 drop of dimethylformamide is added and the mixture is stirred at room temperature for 2 h. The mixture is then concentrated under reduced pressure and the residue is dissolved in 1 ml of dichloromethane and added dropwise to a solution of 119 mg of 5-methylamino-3-trichloromethyl-1,2,4-thiadiazol, 92 mg of ethyl diisopropylamine and 6.2 mg of 4-dimethylaminopyridine in 5 ml of dichloromethane, and the reaction mixture is stirred at room temperature for 20 h. The mixture is then diluted with 15 ml of ethyl acetate, washed with 15 ml of saturated sodium bicarbonate solution and 15 ml of saturated sodium chloride solution, dried over magnesium sulphate, filtered and concentrated under reduced pressure, and the residue is chromatographed over a silica gel column using hexane/ethyl acetate (4:1), giving the product of melting point 122–4° C.

Analogously to the procedure described above, it is also possible to prepare the substances mentioned in the tables below. The melting points are stated in ° C. Ph denotes phenyl.

TABLE 1

| Nr. | $X_1$ | $X_2$ | $R_1$ | $R_2$ | $(R_4)$ | phys. data |
|---|---|---|---|---|---|---|
| 1.1 | N | N | Cl | H | H | |
| 1.2 | N | N | Cl | H | 1-$CH_3$ | |
| 1.3 | N | N | Cl | H | 1-$CH_3$, 3-$CF_3$, 4-Cl | |
| 1.4 | N | N | Cl | H | 1-t-$C_4H_9$, 3-$CH_3$ | |
| 1.5 | N | N | Cl | H | 1-$CH_2$Ph, 3-t-$C_4H_9$ | |
| 1.6 | N | N | Cl | H | 3-t-$C_4H_9$, 1-$CH_3$ | |
| 1.7 | N | N | Cl | H | 1-$C_2H_5$, 3-$CH_3$, 4-$NO_2$ | |
| 1.8 | N | N | Cl | H | 1-$C_2H_5$, 3-$CH_3$, 4-Br | |
| 1.9 | N | N | Cl | $CH_3$ | H | |
| 1.10 | N | N | Cl | $CH_3$ | 1-$CH_3$ | |
| 1.11 | N | N | Cl | $CH_3$ | 1-$CH_3$, 3-$CF_3$, 4-Cl | |
| 1.12 | N | N | Cl | $CH_3$ | 1-t-$C_4H_9$, 3-$CH_3$ | |
| 1.13 | N | N | Cl | $CH_3$ | 1-$CH_2$Ph, 3-t-$C_4H_9$ | |
| 1.14 | N | N | Cl | $CH_3$ | 3-t-$C_4H_9$, 1-$CH_3$ | |
| 1.15 | N | N | Cl | $CH_3$ | 1-$C_2H_5$, 3-$CH_3$, 4-$NO_2$ | |
| 1.16 | N | N | Cl | $CH_3$ | 1-$C_2H_5$, 3-$CH_3$, 4-Br | |
| 1.17 | N | N | Cl | $CH_2CH_2$Ph | H | |
| 1.18 | N | N | Cl | $CH_2CH_2$Ph | 1-$CH_3$ | |
| 1.19 | N | N | Cl | $CH_2CH_2$Ph | 1-$CH_3$, 3-$CF_3$, 4-Cl | m.p. 134–6° |
| 1.20 | N | N | Cl | $CH_2CH_2$Ph | 1-t-$C_4H_9$, 3-$CH_3$ | |
| 1.21 | N | N | Cl | $CH_2CH_2$Ph | 1-$CH_2$Ph, 3-t-$C_4H_9$ | |
| 1.22 | N | N | Cl | $CH_2CH_2$Ph | 3-t-$C_4H_9$, 1-$CH_3$ | |
| 1.23 | N | N | Cl | $CH_2CH_2$Ph | 1-$C_2H_5$, 3-$CH_3$, 4-$NO_2$ | |
| 1.24 | N | N | Cl | $CH_2CH_2$Ph | 1-$C_2H_5$, 3-$CH_3$, 4-Br | |
| 1.25 | N | N | $CF_3$ | H | H | |
| 1.26 | N | N | $CF_3$ | H | 1-$CH_3$ | |
| 1.27 | N | N | $CF_3$ | H | 1-$CH_3$, 3-$CF_3$, 4-Cl | |
| 1.28 | N | N | $CF_3$ | H | 1-t-$C_4H_9$, 3-$CH_3$ | |
| 1.29 | N | N | $CF_3$ | H | 1-$CH_2$Ph, 3-t-$C_4H_9$ | |
| 1.30 | N | N | $CF_3$ | H | 3-t-$C_4H_9$, 1-$CH_3$ | |
| 1.31 | N | N | $CF_3$ | H | 1-$C_2H_5$, 3-$CH_3$, 4-$NO_2$ | |
| 1.32 | N | N | $CF_3$ | H | 1-$C_2H_5$, 3-$CH_3$, 4-Br | |
| 1.33 | N | N | $CF_3$ | $CH_3$ | H | |
| 1.34 | N | N | $CF_3$ | $CH_3$ | 1-$CH_3$ | |
| 1.35 | N | N | $CF_3$ | $CH_3$ | 1-$CH_3$, 3-$CF_3$, 4-Cl | |
| 1.36 | N | N | $CF_3$ | $CH_3$ | 1-t-$C_4H_9$, 3-$CH_3$ | |
| 1.37 | N | N | $CF_3$ | $CH_3$ | 1-$CH_2$Ph, 3-t-$C_4H_9$ | |

TABLE 1-continued

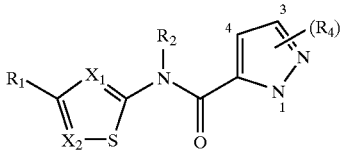

| Nr. | $X_1$ | $X_2$ | $R_1$ | $R_2$ | $(R_4)$ | phys. data |
|---|---|---|---|---|---|---|
| 1.38 | N | N | $CF_3$ | $CH_3$ | 3-t-$C_4H_9$, 1-$CH_3$ | |
| 1.39 | N | N | $CF_3$ | $CH_3$ | 1-$C_2H_5$, 3-$CH_3$, 4-$NO_2$ | |
| 1.40 | N | N | $CF_3$ | $CH_3$ | 1-$C_2H_5$, 3-$CH_3$, 4-Br | |
| 1.41 | N | N | $CF_3$ | $CH_2CH_2Ph$ | H | |
| 1.42 | N | N | $CF_3$ | $CH_2CH_2Ph$ | 1-$CH_3$ | |
| 1.43 | N | N | $CF_3$ | $CH_2CH_2Ph$ | 1-$CH_3$, 3-$CF_3$, 4-Cl | |
| 1.44 | N | N | $CF_3$ | $CH_2CH_2Ph$ | 1-t-$C_4H_9$, 3-$CH_3$ | |
| 1.45 | N | N | $CF_3$ | $CH_2CH_2Ph$ | 1-$CH_2Ph$, 3-t-$C_4H_9$ | |
| 1.46 | N | N | $CF_3$ | $CH_2CH_2Ph$ | 3-t-$C_4H_9$, 1-$CH_3$ | |
| 1.47 | N | N | $CF_3$ | $CH_2CH_2Ph$ | 1-$C_2H_5$, 3-$CH_3$, 4-$NO_2$ | |
| 1.48 | N | N | $CF_3$ | $CH_2CH_2Ph$ | 1-$C_2H_5$, 3-$CH_3$, 4-Br | |
| 1.49 | N | N | $CCl_3$ | H | H | |
| 1.50 | N | N | $CCl_3$ | H | 1-$CH_3$ | |
| 1.51 | N | N | $CCl_3$ | H | 1-$CH_3$, 3-$CF_3$, 4-Cl | m.p. 134–6° |
| 1.52 | N | N | $CCl_3$ | H | 1-t-$C_4H_9$, 3-$CH_3$ | |
| 1.53 | N | N | $CCl_3$ | H | 1-$CH_2Ph$, 3-t-$C_4H_9$ | |
| 1.54 | N | N | $CCl_3$ | H | 3-t-$C_4H_9$, 1-$CH_3$ | |
| 1.55 | N | N | $CCl_3$ | H | 1-$C_2H_5$, 3-$CH_3$, 4-$NO_2$ | |
| 1.56 | N | N | $CCl_3$ | H | 1-$C_2H_5$, 3-$CH_3$, 4-Br | |
| 1.57 | N | N | $CCl_3$ | $CH_3$ | H | |
| 1.58 | N | N | $CCl_3$ | $CH_3$ | 1-$CH_3$ | |
| 1.59 | N | N | $CCl_3$ | $CH_3$ | 1-$CH_3$, 3-$CF_3$, 4-Cl | m.p. 122–4° |
| 1.60 | N | N | $CCl_3$ | $CH_3$ | 1-t-$C_4H_9$, 3-$CH_3$ | |
| 1.61 | N | N | $CCl_3$ | $CH_3$ | 1-$CH_2Ph$, 3-t-$C_4H_9$ | |
| 1.62 | N | N | $CCl_3$ | $CH_3$ | 3-t-$C_4H_9$, 1-$CH_3$ | |
| 1.63 | N | N | $CCl_3$ | $CH_3$ | 1-$C_2H_5$, 3-$CH_3$, 4-$NO_2$ | |
| 1.64 | N | N | $CCl_3$ | $CH_3$ | 1-$C_2H_5$, 3-$CH_3$, 4-Br | |
| 1.65 | N | N | $CCl_3$ | $CH_2CH_2Ph$ | H | |
| 1.66 | N | N | $CCl_3$ | $CH_2CH_2Ph$ | 1-$CH_3$ | |
| 1.67 | N | N | $CCl_3$ | $CH_2CH_2Ph$ | 1-$CH_3$, 3-$CF_3$, 4-Cl | |
| 1.68 | N | N | $CCl_3$ | $CH_2CH_2Ph$ | 1-t-$C_4H_9$, 3-$CH_3$ | |
| 1.69 | N | N | $CCl_3$ | $CH_2CH_2Ph$ | 1-$CH_2Ph$, 3-t-$C_4H_9$ | |
| 1.70 | N | N | $CCl_3$ | $CH_2CH_2Ph$ | 3-t-$C_4H_9$, 1-$CH_3$ | |
| 1.71 | N | N | $CCl_3$ | $CH_2CH_2Ph$ | 1-$C_2H_5$, 3-$CH_3$, 4-$NO_2$ | |
| 1.72 | N | N | $CCl_3$ | $CH_2CH_2Ph$ | 1-$C_2H_5$, 3-$CH_3$, 4-Br | |
| 1.73 | N | N | Ph | H | H | |
| 1.74 | N | N | Ph | H | 1-$CH_3$ | |
| 1.75 | N | N | Ph | H | 1-$CH_3$, 3-$CF_3$, 4-Cl | |
| 1.76 | N | N | Ph | H | 1-t-$C_4H_9$, 3-$CH_3$ | |
| 1.77 | N | N | Ph | H | 1-$CH_2Ph$, 3-t-$C_4H_9$ | |
| 1.78 | N | N | Ph | H | 3-t-$C_4H_9$, 1-$CH_3$ | |
| 1.79 | N | N | Ph | H | 1-$C_2H_5$, 3-$CH_3$, 4-$NO_2$ | |
| 1.80 | N | N | Ph | H | 1-$C_2H_5$, 3-$CH_3$, 4-Br | m.p. 159–61° |
| 1.81 | N | N | Ph | $CH_3$ | H | |
| 1.82 | N | N | Ph | $CH_3$ | 1-$CH_3$ | |
| 1.83 | N | N | Ph | $CH_3$ | 1-$CH_3$, 3-$CF_3$, 4-Cl | |
| 1.84 | N | N | Ph | $CH_3$ | 1-t-$C_4H_9$, 3-$CH_3$ | |
| 1.85 | N | N | Ph | $CH_3$ | 1-$CH_2Ph$, 3-t-$C_4H_9$ | |
| 1.86 | N | N | Ph | $CH_3$ | 3-t-$C_4H_9$, 1-$CH_3$ | |
| 1.87 | N | N | Ph | $CH_3$ | 1-$C_2H_5$, 3-$CH_3$, 4-$NO_2$ | |
| 1.88 | N | N | Ph | $CH_3$ | 1-$C_2H_5$, 3-$CH_3$, 4-Br | |
| 1.89 | N | N | Ph | $CH_2CH_2Ph$ | H | |
| 1.90 | N | N | Ph | $CH_2CH_2Ph$ | 1-$CH_3$ | |
| 1.91 | N | N | Ph | $CH_2CH_2Ph$ | 1-$CH_3$, 3-$CF_3$, 4-Cl | |
| 1.92 | N | N | Ph | $CH_2CH_2Ph$ | 1-t-$C_4H_9$, 3-$CH_3$ | |
| 1.93 | N | N | Ph | $CH_2CH_2Ph$ | 1-$CH_2Ph$, 3-t-$C_4H_9$ | |
| 1.94 | N | N | Ph | $CH_2CH_2Ph$ | 3-t-$C_4H_9$, 1-$CH_3$ | |
| 1.95 | N | N | Ph | $CH_2CH_2Ph$ | 1-$C_2H_5$, 3-$CH_3$, 4-$NO_2$ | |
| 1.96 | N | N | Ph | $CH_2CH_2Ph$ | 1-$C_2H_5$, 3-$CH_3$, 4-Br | |
| 1.97 | N | C(CN) | Cl | H | H | |
| 1.98 | N | C(CN) | Cl | H | 1-$CH_3$ | |
| 1.99 | N | C(CN) | Cl | H | 1-$CH_3$, 3-$CF_3$, 4-Cl | m.p. 141–3° |
| 1.100 | N | C(CN) | Cl | H | 1-t-$C_4H_9$, 3-$CH_3$ | |
| 1.101 | N | C(CN) | Cl | H | 1-$CH_2Ph$, 3-t-$C_4H_9$ | |
| 1.102 | N | C(CN) | Cl | H | 3-t-$C_4H_9$, 1-$CH_3$ | |
| 1.103 | N | C(CN) | Cl | H | 1-$C_2H_5$, 3-$CH_3$, 4-$NO_2$ | |
| 1.104 | N | C(CN) | Cl | H | 1-$C_2H_5$, 3-$CH_3$, 4-Br | |
| 1.105 | N | C(CN) | Cl | $CH_3$ | H | |

TABLE 1-continued

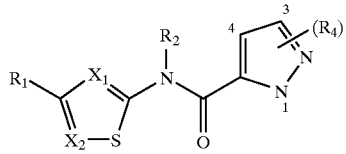

| Nr. | X₁ | X₂ | R₁ | R₂ | (R₄) | phys. data |
|---|---|---|---|---|---|---|
| 1.106 | N | C(CN) | Cl | CH₃ | 1-CH₃ | |
| 1.107 | N | C(CN) | Cl | CH₃ | 1-CH₃, 3-CF₃, 4-Cl | |
| 1.108 | N | C(CN) | Cl | CH₃ | 1-t-C₄H₉, 3-CH₃ | |
| 1.109 | N | C(CN) | Cl | CH₃ | 1-CH₂Ph, 3-t-C₄H₉ | |
| 1.110 | N | C(CN) | Cl | CH₃ | 3-t-C₄H₉, 1-CH₃ | |
| 1.111 | N | C(CN) | Cl | CH₃ | 1-C₂H₅, 3-CH₃, 4-NO₂ | |
| 1.112 | N | C(CN) | Cl | CH₃ | 1-C₂H₅, 3-CH₃, 4-Br | |
| 1.113 | N | C(CN) | Cl | CH₂CH₂Ph | H | |
| 1.114 | N | C(CN) | Cl | CH₂CH₂Ph | 1-CH₃ | |
| 1.115 | N | C(CN) | Cl | CH₂CH₂Ph | 1-CH₃, 3-CF₃, 4-Cl | |
| 1.116 | N | C(CN) | Cl | CH₂CH₂Ph | 1-t-C₄H₉, 3-CH₃ | |
| 1.117 | N | C(CN) | Cl | CH₂CH₂Ph | 1-CH₂Ph, 3-t-C₄H₉ | |
| 1.118 | N | C(CN) | Cl | CH₂CH₂Ph | 3-t-C₄H₉, 1-CH₃ | |
| 1.119 | N | C(CN) | Cl | CH₂CH₂Ph | 1-C₂H₅, 3-CH₃, 4-NO₂ | |
| 1.120 | N | C(CN) | Cl | CH₂CH₂Ph | 1-C₂H₅, 3-CH₃, 4-Br | |
| 1.121 | N | C(CN) | CF₃ | H | H | |
| 1.122 | N | C(CN) | CF₃ | H | 1-CH₃ | |
| 1.123 | N | C(CN) | CF₃ | H | 1-CH₃, 3-CF₃, 4-Cl | m.p. 133–5° |
| 1.124 | N | C(CN) | CF₃ | H | 1-t-C₄H₉, 3-CH₃ | |
| 1.125 | N | C(CN) | CF₃ | H | 1-CH₂Ph, 3-t-C₄H₉ | |
| 1.126 | N | C(CN) | CF₃ | H | 3-t-C₄H₉, 1-CH₃ | |
| 1.127 | N | C(CN) | CF₃ | H | 1-C₂H₅, 3-CH₃, 4-NO₂ | |
| 1.128 | N | C(CN) | CF₃ | H | 1-C₂H₅, 3-CH₃, 4-Br | |
| 1.129 | N | C(CN) | CF₃ | CH₃ | H | |
| 1.130 | N | C(CN) | CF₃ | CH₃ | 1-CH₃ | |
| 1.131 | N | C(CN) | CF₃ | CH₃ | 1-CH₃, 3-CF₃, 4-Cl | |
| 1.132 | N | C(CN) | CF₃ | CH₃ | 1-t-C₄H₉, 3-CH₃ | |
| 1.133 | N | C(CN) | CF₃ | CH₃ | 1-CH₂Ph, 3-t-C₄H₉ | |
| 1.134 | N | C(CN) | CF₃ | CH₃ | 3-t-C₄H₉, 1-CH₃ | |
| 1.135 | N | C(CN) | CF₃ | CH₃ | 1-C₂H₅, 3-CH₃, 4-NO₂ | |
| 1.136 | N | C(CN) | CF₃ | CH₃ | 1-C₂H₅, 3-CH₃, 4-Br | |
| 1.137 | N | C(CN) | CF₃ | CH₂CH₂Ph | H | |
| 1.138 | N | C(CN) | CF₃ | CH₂CH₂Ph | 1-CH₃ | |
| 1.139 | N | C(CN) | CF₃ | CH₂CH₂Ph | 1-CH₃, 3-CF₃, 4-Cl | |
| 1.140 | N | C(CN) | CF₃ | CH₂CH₂Ph | 1-t-C₄H₉, 3-CH₃ | |
| 1.141 | N | C(CN) | CF₃ | CH₂CH₂Ph | 1-CH₂Ph, 3-t-C₄H₉ | |
| 1.142 | N | C(CN) | CF₃ | CH₂CH₂Ph | 3-t-C₄H₉, 1-CH₃ | |
| 1.143 | N | C(CN) | CF₃ | CH₂CH₂Ph | 1-C₂H₅, 3-CH₃, 4-NO₂ | |
| 1.144 | N | C(CN) | CF₃ | CH₂CH₂Ph | 1-C₂H₅, 3-CH₃, 4-Br | |
| 1.145 | N | C(CN) | CCl₃ | H | H | |
| 1.146 | N | C(CN) | CCl₃ | H | 1-CH₃ | |
| 1.147 | N | C(CN) | CCl₃ | H | 1-CH₃, 3-CF₃, 4-Cl | |
| 1.148 | N | C(CN) | CCl₃ | H | 1-t-C₄H₉, 3-CH₃ | |
| 1.149 | N | C(CN) | CCl₃ | H | 1-CH₂Ph, 3-t-C₄H₉ | |
| 1.150 | N | C(CN) | CCl₃ | H | 3-t-C₄H₉, 1-CH₃ | |
| 1.151 | N | C(CN) | CCl₃ | H | 1-C₂H₅, 3-CH₃, 4-NO₂ | |
| 1.152 | N | C(CN) | CCl₃ | H | 1-C₂H₅, 3-CH₃, 4-Br | |
| 1.153 | N | C(CN) | CCl₃ | CH₃ | H | |
| 1.154 | N | C(CN) | CCl₃ | CH₃ | 1-CH₃ | |
| 1.155 | N | C(CN) | CCl₃ | CH₃ | 1-CH₃, 3-CF₃, 4-Cl | |
| 1.156 | N | C(CN) | CCl₃ | CH₃ | 1-t-C₄H₉, 3-CH₃ | |
| 1.157 | N | C(CN) | CCl₃ | CH₃ | 1-CH₂Ph, 3-t-C₄H₉ | |
| 1.158 | N | C(CN) | CCl₃ | CH₃ | 3-t-C₄H₉, 1-CH₃ | |
| 1.159 | N | C(CN) | CCl₃ | CH₃ | 1-C₂H₅, 3-CH₃, 4-NO₂ | |
| 1.160 | N | C(CN) | CCl₃ | CH₃ | 1-C₂H₅, 3-CH₃, 4-Br | |
| 1.161 | N | C(CN) | CCl₃ | CH₂CH₂Ph | H | |
| 1.162 | N | C(CN) | CCl₃ | CH₂CH₂Ph | 1-CH₃ | |
| 1.163 | N | C(CN) | CCl₃ | CH₂CH₂Ph | 1-CH₃, 3-CF₃, 4-Cl | |
| 1.164 | N | C(CN) | CCl₃ | CH₂CH₂Ph | 1-t-C₄H₉, 3-CH₃ | |
| 1.165 | N | C(CN) | CCl₃ | CH₂CH₂Ph | 1-CH₂Ph, 3-t-C₄H₉ | |
| 1.166 | N | C(CN) | CCl₃ | CH₂CH₂Ph | 3-t-C₄H₉, 1-CH₃ | |
| 1.167 | N | C(CN) | CCl₃ | CH₂CH₂Ph | 1-C₂H₅, 3-CH₃, 4-NO₂ | |
| 1.168 | N | C(CN) | CCl₃ | CH₂CH₂Ph | 1-C₂H₅, 3-CH₃, 4-Br | |
| 1.169 | N | C(CN) | Ph | H | H | |
| 1.170 | N | C(CN) | Ph | H | 1-CH₃ | |
| 1.171 | N | C(CN) | Ph | H | 1-CH₃, 3-CF₃, 4-Cl | |
| 1.172 | N | C(CN) | Ph | H | 1-t-C₄H₉, 3-CH₃ | |
| 1.173 | N | C(CN) | Ph | H | 1-CH₂Ph, 3-t-C₄H₉ | |

TABLE 1-continued

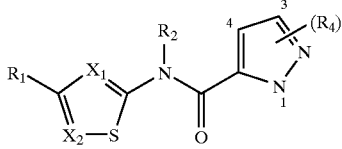

| Nr. | X₁ | X₂ | R₁ | R₂ | (R₄) | phys. data |
|---|---|---|---|---|---|---|
| 1.174 | N | C(CN) | Ph | H | 3-t-C₄H₉, 1-CH₃ | |
| 1.175 | N | C(CN) | Ph | H | 1-C₂H₅, 3-CH₃, 4-NO₂ | |
| 1.176 | N | C(CN) | Ph | H | 1-C₂H₅, 3-CH₃, 4-Br | |
| 1.177 | N | C(CN) | Ph | CH₃ | H | |
| 1.178 | N | C(CN) | Ph | CH₃ | 1-CH₃ | |
| 1.179 | N | C(CN) | Ph | CH₃ | 1-CH₃, 3-CF₃, 4-Cl | |
| 1.180 | N | C(CN) | Ph | CH₃ | 1-t-C₄H₉, 3-CH₃ | |
| 1.181 | N | C(CN) | Ph | CH₃ | 1-CH₂Ph, 3-t-C₄H₉ | |
| 1.182 | N | C(CN) | Ph | CH₃ | 3-t-C₄H₉, 1-CH₃ | |
| 1.183 | N | C(CN) | Ph | CH₃ | 1-C₂H₅, 3-CH₃, 4-NO₂ | |
| 1.184 | N | C(CN) | Ph | CH₃ | 1-C₂H₅, 3-CH₃, 4-Br | |
| 1.185 | N | C(CN) | Ph | CH₂CH₂Ph | H | |
| 1.186 | N | C(CN) | Ph | CH₂CH₂Ph | 1-CH₃ | |
| 1.187 | N | C(CN) | Ph | CH₂CH₂Ph | 1-CH₃, 3-CF₃, 4-Cl | |
| 1.188 | N | C(CN) | Ph | CH₂CH₂Ph | 1-t-C₄H₉, 3-CH₃ | |
| 1.189 | N | C(CN) | Ph | CH₂CH₂Ph | 1-CH₂Ph, 3-t-C₄H₉ | |
| 1.190 | N | C(CN) | Ph | CH₂CH₂Ph | 3-t-C₄H₉, 1-CH₃ | |
| 1.191 | N | C(CN) | Ph | CH₂CH₂Ph | 1-C₂H₅, 3-CH₃, 4-NO₂ | |
| 1.192 | N | C(CN) | Ph | CH₂CH₂Ph | 1-C₂H₅, 3-CH₃, 4-Br | |
| 1.193 | C(CN) | N | Cl | H | H | |
| 1.194 | C(CN) | N | Cl | H | 1-CH₃ | |
| 1.195 | C(CN) | N | Cl | H | 1-CH₃, 3-CF₃, 4-Cl | |
| 1.196 | C(CN) | N | Cl | H | 1-t-C₄H₉, 3-CH₃ | |
| 1.197 | C(CN) | N | Cl | H | 1-CH₂Ph, 3-t-C₄H₉ | |
| 1.198 | C(CN) | N | Cl | H | 3-t-C₄H₉, 1-CH₃ | |
| 1.199 | C(CN) | N | Cl | H | 1-C₂H₅, 3-CH₃, 4-NO₂ | |
| 1.200 | C(CN) | N | Cl | H | 1-C₂H₅, 3-CH₃, 4-Br | |
| 1.201 | C(CN) | N | Cl | CH₃ | H | |
| 1.202 | C(CN) | N | Cl | CH₃ | 1-CH₃ | |
| 1.203 | C(CN) | N | Cl | CH₃ | 1-CH₃, 3-CF₃, 4-Cl | |
| 1.204 | C(CN) | N | Cl | CH₃ | 1-t-C₄H₉, 3-CH₃ | |
| 1.205 | C(CN) | N | Cl | CH₃ | 1-CH₂Ph, 3-t-C₄H₉ | |
| 1.206 | C(CN) | N | Cl | CH₃ | 3-t-C₄H₉, 1-CH₃ | |
| 1.207 | C(CN) | N | Cl | CH₃ | 1-C₂H₅, 3-CH₃, 4-NO₂ | |
| 1.208 | C(CN) | N | Cl | CH₃ | 1-C₂H₅, 3-CH₃, 4-Br | |
| 1.209 | C(CN) | N | Cl | CH₂CH₂Ph | H | |
| 1.210 | C(CN) | N | Cl | CH₂CH₂Ph | 1-CH₃ | |
| 1.211 | C(CN) | N | Cl | CH₂CH₂Ph | 1-CH₃, 3-CF₃, 4-Cl | |
| 1.212 | C(CN) | N | Cl | CH₂CH₂Ph | 1-t-C₄H₉, 3-CH₃ | |
| 1.213 | C(CN) | N | Cl | CH₂CH₂Ph | 1-CH₂Ph, 3-t-C₄H₉ | |
| 1.214 | C(CN) | N | Cl | CH₂CH₂Ph | 3-t-C₄H₉, 1-CH₃ | |
| 1.215 | C(CN) | N | Cl | CH₂CH₂Ph | 1-C₂H₅, 3-CH₃, 4-NO₂ | |
| 1.216 | C(CN) | N | Cl | CH₂CH₂Ph | 1-C₂H₅, 3-CH₃, 4-Br | |
| 1.217 | C(CN) | N | CF₃ | H | H | |
| 1.218 | C(CN) | N | CF₃ | H | 1-CH₃ | |
| 1.219 | C(CN) | N | CF₃ | H | 1-CH₃, 3-CF₃, 4-Cl | |
| 1.220 | C(CN) | N | CF₃ | H | 1-t-C₄H₉, 3-CH₃ | |
| 1.221 | C(CN) | N | CF₃ | H | 1-CH₂Ph, 3-t-C₄H₉ | |
| 1.222 | C(CN) | N | CF₃ | H | 3-t-C₄H₉, 1-CH₃ | |
| 1.223 | C(CN) | N | CF₃ | H | 1-C₂H₅, 3-CH₃, 4-NO₂ | |
| 1.224 | C(CN) | N | CF₃ | H | 1-C₂H₅, 3-CH₃, 4-Br | |
| 1.225 | C(CN) | N | CF₃ | CH₃ | H | |
| 1.226 | C(CN) | N | CF₃ | CH₃ | 1-CH₃ | |
| 1.227 | C(CN) | N | CF₃ | CH₃ | 1-CH₃, 3-CF₃, 4-Cl | |
| 1.228 | C(CN) | N | CF₃ | CH₃ | 1-t-C₄H₉, 3-CH₃ | |
| 1.229 | C(CN) | N | CF₃ | CH₃ | 1-CH₂Ph, 3-t-C₄H₉ | |
| 1.230 | C(CN) | N | CF₃ | CH₃ | 3-t-C₄H₉, 1-CH₃ | |
| 1.231 | C(CN) | N | CF₃ | CH₃ | 1-C₂H₅, 3-CH₃, 4-NO₂ | |
| 1.232 | C(CN) | N | CF₃ | CH₃ | 1-C₂H₅, 3-CH₃, 4-Br | |
| 1.233 | C(CN) | N | CF₃ | CH₂CH₂Ph | H | |
| 1.234 | C(CN) | N | CF₃ | CH₂CH₂Ph | 1-CH₃ | |
| 1.235 | C(CN) | N | CF₃ | CH₂CH₂Ph | 1-CH₃, 3-CF₃, 4-Cl | |
| 1.236 | C(CN) | N | CF₃ | CH₂CH₂Ph | 1-t-C₄H₉, 3-CH₃ | |
| 1.237 | C(CN) | N | CF₃ | CH₂CH₂Ph | 1-CH₂Ph, 3-t-C₄H₉ | |
| 1.238 | C(CN) | N | CF₃ | CH₂CH₂Ph | 3-t-C₄H₉, 1-CH₃ | |
| 1.239 | C(CN) | N | CF₃ | CH₂CH₂Ph | 1-C₂H₅, 3-CH₃, 4-NO₂ | |
| 1.240 | C(CN) | N | CF₃ | CH₂CH₂Ph | 1-C₂H₅, 3-CH₃, 4-Br | |
| 1.241 | C(CN) | N | CCl₃ | H | H | |

TABLE 1-continued

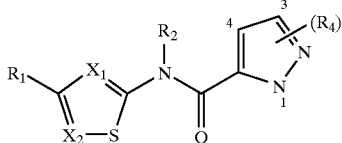

| Nr. | X₁ | X₂ | R₁ | R₂ | (R₄) | phys. data |
|---|---|---|---|---|---|---|
| 1.242 | C(CN) | N | CCl₃ | H | 1-CH₃ | |
| 1.243 | C(CN) | N | CCl₃ | H | 1-CH₃, 3-CF₃, 4-Cl | |
| 1.244 | C(CN) | N | CCl₃ | H | 1-t-C₄H₉, 3-CH₃ | |
| 1.245 | C(CN) | N | CCl₃ | H | 1-CH₂Ph, 3-t-C₄H₉ | |
| 1.246 | C(CN) | N | CCl₃ | H | 3-t-C₄H₉, 1-CH₃ | |
| 1.247 | C(CN) | N | CCl₃ | H | 1-C₂H₅, 3-CH₃, 4-NO₂ | |
| 1.248 | C(CN) | N | CCl₃ | H | 1-C₂H₅, 3-CH₃, 4-Br | |
| 1.249 | C(CN) | N | CCl₃ | CH₃ | H | |
| 1.250 | C(CN) | N | CCl₃ | CH₃ | 1-CH₃ | |
| 1.251 | C(CN) | N | CCl₃ | CH₃ | 1-CH₃, 3-CF₃, 4-Cl | |
| 1.252 | C(CN) | N | CCl₃ | CH₃ | 1-t-C₄H₉, 3-CH₃ | |
| 1.253 | C(CN) | N | CCl₃ | CH₃ | 1-CH₂Ph, 3-t-C₄H₉ | |
| 1.254 | C(CN) | N | CCl₃ | CH₃ | 3-t-C₄H₉, 1-CH₃ | |
| 1.255 | C(CN) | N | CCl₃ | CH₃ | 1-C₂H₅, 3-CH₃, 4-NO₂ | |
| 1.256 | C(CN) | N | CCl₃ | CH₃ | 1-C₂H₅, 3-CH₃, 4-Br | |
| 1.257 | C(CN) | N | CCl₃ | CH₂CH₂Ph | H | |
| 1.258 | C(CN) | N | CCl₃ | CH₂CH₂Ph | 1-CH₃ | |
| 1.259 | C(CN) | N | CCl₃ | CH₂CH₂Ph | 1-CH₃, 3-CF₃, 4-Cl | |
| 1.260 | C(CN) | N | CCl₃ | CH₂CH₂Ph | 1-t-C₄H₉, 3-CH₃ | |
| 1.261 | C(CN) | N | CCl₃ | CH₂CH₂Ph | 1-CH₂Ph, 3-t-C₄H₉ | |
| 1.262 | C(CN) | N | CCl₃ | CH₂CH₂Ph | 3-t-C₄H₉, 1-CH₃ | |
| 1.263 | C(CN) | N | CCl₃ | CH₂CH₂Ph | 1-C₂H₅, 3-CH₃, 4-NO₂ | |
| 1.264 | C(CN) | N | CCl₃ | CH₂CH₂Ph | 1-C₂H₅, 3-CH₃, 4-Br | |
| 1.265 | C(CN) | N | Ph | H | H | |
| 1.266 | C(CN) | N | Ph | H | 1-CH₃ | |
| 1.267 | C(CN) | N | Ph | H | 1-CH₃, 3-CF₃, 4-Cl | |
| 1.268 | C(CN) | N | Ph | H | 1-t-C₄H₉, 3-CH₃ | |
| 1.269 | C(CN) | N | Ph | H | 1-CH₂Ph, 3-t-C₄H₉ | |
| 1.270 | C(CN) | N | Ph | H | 3-t-C₄H₉, 1-CH₃ | |
| 1.271 | C(CN) | N | Ph | H | 1-C₂H₅, 3-CH₃, 4-NO₂ | |
| 1.272 | C(CN) | N | Ph | H | 1-C₂H₅, 3-CH₃, 4-Br | |
| 1.273 | C(CN) | N | Ph | CH₃ | H | |
| 1.274 | C(CN) | N | Ph | CH₃ | 1-CH₃ | |
| 1.275 | C(CN) | N | Ph | CH₃ | 1-CH₃, 3-CF₃, 4-Cl | |
| 1.276 | C(CN) | N | Ph | CH₃ | 1-t-C₄H₉, 3-CH₃ | |
| 1.277 | C(CN) | N | Ph | CH₃ | 1-CH₂Ph, 3-t-C₄H₉ | |
| 1.278 | C(CN) | N | Ph | CH₃ | 3-t-C₄H₉, 1-CH₃ | |
| 1.279 | C(CN) | N | Ph | CH₃ | 1-C₂H₅, 3-CH₃, 4-NO₂ | |
| 1.280 | C(CN) | N | Ph | CH₃ | 1-C₂H₅, 3-CH₃, 4-Br | |
| 1.281 | C(CN) | N | Ph | CH₂CH₂Ph | H | |
| 1.282 | C(CN) | N | Ph | CH₂CH₂Ph | 1-CH₃ | |
| 1.283 | C(CN) | N | Ph | CH₂CH₂Ph | 1-CH₃, 3-CF₃, 4-Cl | |
| 1.284 | C(CN) | N | Ph | CH₂CH₂Ph | 1-t-C₄H₉, 3-CH₃ | |
| 1.285 | C(CN) | N | Ph | CH₂CH₂Ph | 1-CH₂Ph, 3-t-C₄H₉ | |
| 1.286 | C(CN) | N | Ph | CH₂CH₂Ph | 3-t-C₄H₉, 1-CH₃ | |
| 1.287 | C(CN) | N | Ph | CH₂CH₂Ph | 1-C₂H₅, 3-CH₃, 4-NO₂ | |
| 1.288 | C(CN) | N | Ph | CH₂CH₂Ph | 1-C₂H₅, 3-CH₃, 4-Br | |
| 1.289 | C(CN) | C(CN) | Cl | H | H | |
| 1.290 | C(CN) | C(CN) | Cl | H | 1-CH₃ | |
| 1.291 | C(CN) | C(CN) | Cl | H | 1-CH₃, 3-CF₃, 4-Cl | |
| 1.292 | C(CN) | C(CN) | Cl | H | 1-t-C₄H₉, 3-CH₃ | |
| 1.293 | C(CN) | C(CN) | Cl | H | 1-CH₂Ph, 3-t-C₄H₉ | |
| 1.294 | C(CN) | C(CN) | Cl | H | 3-t-C₄H₉, 1-CH₃ | |
| 1.295 | C(CN) | C(CN) | Cl | H | 1-C₂H₅, 3-CH₃, 4-NO₂ | |
| 1.296 | C(CN) | C(CN) | Cl | H | 1-C₂H₅, 3-CH₃, 4-Br | |
| 1.297 | C(CN) | C(CN) | Cl | CH₃ | H | |
| 1.298 | C(CN) | C(CN) | Cl | CH₃ | 1-CH₃ | |
| 1.299 | C(CN) | C(CN) | Cl | CH₃ | 1-CH₃, 3-CF₃, 4-Cl | |
| 1.300 | C(CN) | C(CN) | Cl | CH₃ | 1-t-C₄H₉, 3-CH₃ | |
| 1.301 | C(CN) | C(CN) | Cl | CH₃ | 1-CH₂Ph, 3-t-C₄H₉ | |
| 1.302 | C(CN) | C(CN) | Cl | CH₃ | 3-t-C₄H₉, 1-CH₃ | |
| 1.303 | C(CN) | C(CN) | Cl | CH₃ | 1-C₂H₅, 3-CH₃, 4-NO₂ | |
| 1.304 | C(CN) | C(CN) | Cl | CH₃ | 1-C₂H₅, 3-CH₃, 4-Br | |
| 1.305 | C(CN) | C(CN) | Cl | CH₂CH₂Ph | H | |
| 1.306 | C(CN) | C(CN) | Cl | CH₂CH₂Ph | 1-CH₃ | |
| 1.307 | C(CN) | C(CN) | Cl | CH₂CH₂Ph | 1-CH₃, 3-CF₃, 4-Cl | |
| 1.308 | C(CN) | C(CN) | Cl | CH₂CH₂Ph | 1-t-C₄H₉, 3-CH₃ | |
| 1.309 | C(CN) | C(CN) | Cl | CH₂CH₂Ph | 1-CH₂Ph, 3-t-C₄H₉ | |

TABLE 1-continued

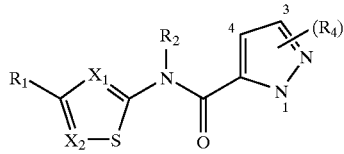

| Nr. | X₁ | X₂ | R₁ | R₂ | (R₄) | phys. data |
|---|---|---|---|---|---|---|
| 1.310 | C(CN) | C(CN) | Cl | CH₂CH₂Ph | 3-t-C₄H₉, 1-CH₃ | |
| 1.311 | C(CN) | C(CN) | Cl | CH₂CH₂Ph | 1-C₂H₅, 3-CH₃, 4-NO₂ | |
| 1.312 | C(CN) | C(CN) | Cl | CH₂CH₂Ph | 1-C₂H₅, 3-CH₃, 4-Br | |
| 1.313 | C(CN) | C(CN) | CF₃ | H | H | |
| 1.314 | C(CN) | C(CN) | CF₃ | H | 1-CH₃ | |
| 1.315 | C(CN) | C(CN) | CF₃ | H | 1-CH₃, 3-CF₃, 4-Cl | |
| 1.316 | C(CN) | C(CN) | CF₃ | H | 1-t-C₄H₉, 3-CH₃ | |
| 1.317 | C(CN) | C(CN) | CF₃ | H | 1-CH₂Ph, 3-t-C₄H₉ | |
| 1.318 | C(CN) | C(CN) | CF₃ | H | 3-t-C₄H₉, 1-CH₃ | |
| 1.319 | C(CN) | C(CN) | CF₃ | H | 1-C₂H₅, 3-CH₃, 4-NO₂ | |
| 1.320 | C(CN) | C(CN) | CF₃ | H | 1-C₂H₅, 3-CH₃, 4-Br | |
| 1.321 | C(CN) | C(CN) | CF₃ | CH₃ | H | |
| 1.322 | C(CN) | C(CN) | CF₃ | CH₃ | 1-CH₃ | |
| 1.323 | C(CN) | C(CN) | CF₃ | CH₃ | 1-CH₃, 3-CF₃, 4-Cl | |
| 1.324 | C(CN) | C(CN) | CF₃ | CH₃ | 1-t-C₄H₉, 3-CH₃ | |
| 1.325 | C(CN) | C(CN) | CF₃ | CH₃ | 1-CH₂Ph, 3-t-C₄H₉ | |
| 1.326 | C(CN) | C(CN) | CF₃ | CH₃ | 3-t-C₄H₉, 1-CH₃ | |
| 1.327 | C(CN) | C(CN) | CF₃ | CH₃ | 1-C₂H₅, 3-CH₃, 4-NO₂ | |
| 1.328 | C(CN) | C(CN) | CF₃ | CH₃ | 1-C₂H₅, 3-CH₃, 4-Br | |
| 1.329 | C(CN) | C(CN) | CF₃ | CH₂CH₂Ph | H | |
| 1.330 | C(CN) | C(CN) | CF₃ | CH₂CH₂Ph | 1-CH₃ | |
| 1.331 | C(CN) | C(CN) | CF₃ | CH₂CH₂Ph | 1-CH₃, 3-CF₃, 4-Cl | |
| 1.332 | C(CN) | C(CN) | CF₃ | CH₂CH₂Ph | 1-t-C₄H₉, 3-CH₃ | |
| 1.333 | C(CN) | C(CN) | CF₃ | CH₂CH₂Ph | 1-CH₂Ph, 3-t-C₄H₉ | |
| 1.334 | C(CN) | C(CN) | CF₃ | CH₂CH₂Ph | 3-t-C₄H₉, 1-CH₃ | |
| 1.335 | C(CN) | C(CN) | CF₃ | CH₂CH₂Ph | 1-C₂H₅, 3-CH₃, 4-NO₂ | |
| 1.336 | C(CN) | C(CN) | CF₃ | CH₂CH₂Ph | 1-C₂H₅, 3-CH₃, 4-Br | |
| 1.337 | C(CN) | C(CN) | CCl₃ | H | H | |
| 1.338 | C(CN) | C(CN) | CCl₃ | H | 1-CH₃ | |
| 1.339 | C(CN) | C(CN) | CCl₃ | H | 1-CH₃, 3-CF₃, 4-Cl | |
| 1.340 | C(CN) | C(CN) | CCl₃ | H | 1-t-C₄H₉, 3-CH₃ | |
| 1.341 | C(CN) | C(CN) | CCl₃ | H | 1-CH₂Ph, 3-t-C₄H₉ | |
| 1.342 | C(CN) | C(CN) | CCl₃ | H | 3-t-C₄H₉, 1-CH₃ | |
| 1.343 | C(CN) | C(CN) | CCl₃ | H | 1-C₂H₅, 3-CH₃, 4-NO₂ | |
| 1.344 | C(CN) | C(CN) | CCl₃ | H | 1-C₂H₅, 3-CH₃, 4-Br | |
| 1.345 | C(CN) | C(CN) | CCl₃ | CH₃ | H | |
| 1.346 | C(CN) | C(CN) | CCl₃ | CH₃ | 1-CH₃ | |
| 1.347 | C(CN) | C(CN) | CCl₃ | CH₃ | 1-CH₃, 3-CF₃, 4-Cl | |
| 1.348 | C(CN) | C(CN) | CCl₃ | CH₃ | 1-t-C₄H₉, 3-CH₃ | |
| 1.349 | C(CN) | C(CN) | CCl₃ | CH₃ | 1-CH₂Ph, 3-t-C₄H₉ | |
| 1.350 | C(CN) | C(CN) | CCl₃ | CH₃ | 3-t-C₄H₉, 1-CH₃ | |
| 1.351 | C(CN) | C(CN) | CCl₃ | CH₃ | 1-C₂H₅, 3-CH₃, 4-NO₂ | |
| 1.352 | C(CN) | C(CN) | CCl₃ | CH₃ | 1-C₂H₅, 3-CH₃, 4-Br | |
| 1.353 | C(CN) | C(CN) | CCl₃ | CH₂CH₂Ph | H | |
| 1.354 | C(CN) | C(CN) | CCl₃ | CH₂CH₂Ph | 1-CH₃ | |
| 1.355 | C(CN) | C(CN) | CCl₃ | CH₂CH₂Ph | 1-CH₃, 3-CF₃, 4-Cl | |
| 1.356 | C(CN) | C(CN) | CCl₃ | CH₂CH₂Ph | 1-t-C₄H₉, 3-CH₃ | |
| 1.357 | C(CN) | C(CN) | CCl₃ | CH₂CH₂Ph | 1-CH₂Ph, 3-t-C₄H₉ | |
| 1.358 | C(CN) | C(CN) | CCl₃ | CH₂CH₂Ph | 3-t-C₄H₉, 1-CH₃ | |
| 1.359 | C(CN) | C(CN) | CCl₃ | CH₂CH₂Ph | 1-C₂H₅, 3-CH₃, 4-NO₂ | |
| 1.360 | C(CN) | C(CN) | CCl₃ | CH₂CH₂Ph | 1-C₂H₅, 3-CH₃, 4-Br | |
| 1.361 | C(CN) | C(CN) | Ph | H | H | |
| 1.362 | C(CN) | C(CN) | Ph | H | 1-CH₃ | |
| 1.363 | C(CN) | C(CN) | Ph | H | 1-CH₃, 3-CF₃, 4-Cl | |
| 1.364 | C(CN) | C(CN) | Ph | H | 1-t-C₄H₉, 3-CH₃ | |
| 1.365 | C(CN) | C(CN) | Ph | H | 1-CH₂Ph, 3-t-C₄H₉ | |
| 1.366 | C(CN) | C(CN) | Ph | H | 3-t-C₄H₉, 1-CH₃ | |
| 1.367 | C(CN) | C(CN) | Ph | H | 1-C₂H₅, 3-CH₃, 4-NO₂ | |
| 1.368 | C(CN) | C(CN) | Ph | H | 1-C₂H₅, 3-CH₃, 4-Br | |
| 1.369 | C(CN) | C(CN) | Ph | CH₃ | H | |
| 1.370 | C(CN) | C(CN) | Ph | CH₃ | 1-CH₃ | |
| 1.371 | C(CN) | C(CN) | Ph | CH₃ | 1-CH₃, 3-CF₃, 4-Cl | |
| 1.372 | C(CN) | C(CN) | Ph | CH₃ | 1-t-C₄H₉, 3-CH₃ | |
| 1.373 | C(CN) | C(CN) | Ph | CH₃ | 1-CH₂Ph, 3-t-C₄H₉ | |
| 1.374 | C(CN) | C(CN) | Ph | CH₃ | 3-t-C₄H₉, 1-CH₃ | |
| 1.375 | C(CN) | C(CN) | Ph | CH₃ | 1-C₂H₅, 3-CH₃, 4-NO₂ | |
| 1.376 | C(CN) | C(CN) | Ph | CH₃ | 1-C₂H₅, 3-CH₃, 4-Br | |
| 1.377 | C(CN) | C(CN) | Ph | CH₂CH₂Ph | H | |

TABLE 1-continued

| Nr. | X₁ | X₂ | R₁ | R₂ | (R₄) | phys. data |
|---|---|---|---|---|---|---|
| 1.378 | C(CN) | C(CN) | Ph | CH₂CH₂Ph | 1-CH₃ | |
| 1.379 | C(CN) | C(CN) | Ph | CH₂CH₂Ph | 1-CH₃, 3-CF₃, 4-Cl | |
| 1.380 | C(CN) | C(CN) | Ph | CH₂CH₂Ph | 1-t-C₄H₉, 3-CH₃ | |
| 1.381 | C(CN) | C(CN) | Ph | CH₂CH₂Ph | 1-CH₂Ph, 3-t-C₄H₉ | |
| 1.382 | C(CN) | C(CN) | Ph | CH₂CH₂Ph | 3-t-C₄H₉, 1-CH₃ | |
| 1.383 | C(CN) | C(CN) | Ph | CH₂CH₂Ph | 1-C₂H₅, 3-CH₃, 4-NO₂ | |
| 1.384 | C(CN) | C(CN) | Ph | CH₂CH₂Ph | 1 C₂H₅, 3-CH₃, 4-Br | |

TABLE 2

| Nr. | X₁ | X₂ | R₁ | R₂ | (R₅) | phys. data |
|---|---|---|---|---|---|---|
| 2.1 | N | N | Cl | H | H | |
| 2.2 | N | N | Cl | H | 2-F | |
| 2.3 | N | N | Cl | H | 2-Cl | |
| 2.4 | N | N | Cl | H | 4-F | |
| 2.5 | N | N | Cl | H | 4-Cl | |
| 2.6 | N | N | Cl | H | 2,4-F₂ | |
| 2.7 | N | N | Cl | H | 2,4-Cl₂ | |
| 2.8 | N | N | Cl | H | 2-F, 4-NO₂, 5-OCH₃ | |
| 2.9 | N | N | Cl | CH₃ | H | |
| 2.10 | N | N | Cl | CH₃ | 2-F | |
| 2.11 | N | N | Cl | CH₃ | 2-Cl | |
| 2.12 | N | N | Cl | CH₃ | 4-F | |
| 2.13 | N | N | Cl | CH₃ | 4-Cl | |
| 2.14 | N | N | Cl | CH₃ | 2,4-F₂ | |
| 2.15 | N | N | Cl | CH₃ | 2,4-Cl₂ | |
| 2.16 | N | N | Cl | CH₃ | 2-F, 4-NO₂, 5-OCH₃ | |
| 2.17 | N | N | Cl | CH₂CH₂Ph | H | |
| 2.18 | N | N | Cl | CH₂CH₂Ph | 2-F | |
| 2.19 | N | N | Cl | CH₂CH₂Ph | 2-Cl | |
| 2.20 | N | N | Cl | CH₂CH₂Ph | 4-F | |
| 2.21 | N | N | Cl | CH₂CH₂Ph | 4-Cl | |
| 2.22 | N | N | Cl | CH₂CH₂Ph | 2,4-F₂ | m.p. 115–7° |
| 2.23 | N | N | Cl | CH₂CH₂Ph | 2,4-Cl₂ | m.p. 75–8° |
| 2.24 | N | N | Cl | CH₂CH₂Ph | 2-F, 4-NO₂, 5-OCH₃ | m.p. 212–4° |
| 2.25 | N | N | CF₃ | H | H | |
| 2.26 | N | N | CF₃ | H | 2-F | |
| 2.27 | N | N | CF₃ | H | 2-Cl | |
| 2.28 | N | N | CF₃ | H | 4-F | |
| 2.29 | N | N | CF₃ | H | 4-Cl | |
| 2.30 | N | N | CF₃ | H | 2,4-F₂ | |
| 2.31 | N | N | CF₃ | H | 2,4-Cl₂ | |
| 2.32 | N | N | CF₃ | H | 2-F, 4-NO₂, 5-OCH₃ | |
| 2.33 | N | N | CF₃ | CH₃ | H | |
| 2.34 | N | N | CF₃ | CH₃ | 2-F | |
| 2.35 | N | N | CF₃ | CH₃ | 2-Cl | |
| 2.36 | N | N | CF₃ | CH₃ | 4-F | |
| 2.37 | N | N | CF₃ | CH₃ | 4-Cl | |
| 2.38 | N | N | CF₃ | CH₃ | 2,4-F₂ | |
| 2.39 | N | N | CF₃ | CH₃ | 2,4-Cl₂ | |
| 2.40 | N | N | CF₃ | CH₃ | 2-F, 4-NO₂, 5-OCH₃ | |
| 2.41 | N | N | CF₃ | CH₂CH₂Ph | H | |
| 2.42 | N | N | CF₃ | CH₂CH₂Ph | 2-F | |

TABLE 2-continued

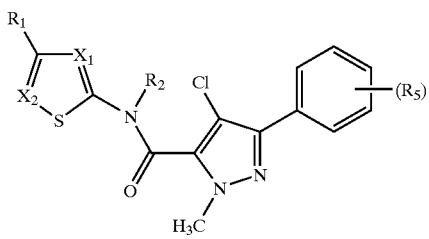

| Nr. | $X_1$ | $X_2$ | $R_1$ | $R_2$ | $(R_5)$ | phys. data |
|---|---|---|---|---|---|---|
| 2.43 | N | N | $CF_3$ | $CH_2CH_2Ph$ | 2-Cl | |
| 2.44 | N | N | $CF_3$ | $CH_2CH_2Ph$ | 4-F | |
| 2.45 | N | N | $CF_3$ | $CH_2CH_2Ph$ | 4-Cl | |
| 2.46 | N | N | $CF_3$ | $CH_2CH_2Ph$ | 2,4-$F_2$ | |
| 2.47 | N | N | $CF_3$ | $CH_2CH_2Ph$ | 2,4-$Cl_2$ | |
| 2.48 | N | N | $CF_3$ | $CH_2CH_2Ph$ | 2-F, 4-$NO_2$, 5-$OCH_3$ | |
| 2.49 | N | N | $CCl_3$ | H | H | |
| 2.50 | N | N | $CCl_3$ | H | 2-F | |
| 2.51 | N | N | $CCl_3$ | H | 2-Cl | |
| 2.52 | N | N | $CCl_3$ | H | 4-F | |
| 2.53 | N | N | $CCl_3$ | H | 4-Cl | |
| 2.54 | N | N | $CCl_3$ | H | 2,4-$F_2$ | m.p. 188–90° |
| 2.55 | N | N | $CCl_3$ | H | 2,4-$Cl_2$ | m.p. 111–3° |
| 2.56 | N | N | $CCl_3$ | H | 2-F, 4-$NO_2$, 5-$OCH_3$ | m.p. 203–4° |
| 2.57 | N | N | $CCl_3$ | $CH_3$ | H | |
| 2.58 | N | N | $CCl_3$ | $CH_3$ | 2-F | |
| 2.59 | N | N | $CCl_3$ | $CH_3$ | 2-Cl | |
| 2.60 | N | N | $CCl_3$ | $CH_3$ | 4-F | |
| 2.61 | N | N | $CCl_3$ | $CH_3$ | 4-Cl | |
| 2.62 | N | N | $CCl_3$ | $CH_3$ | 2,4-$F_2$ | m.p. 67–9° |
| 2.63 | N | N | $CCl_3$ | $CH_3$ | 2,4-$Cl_2$ | |
| 2.64 | N | N | $CCl_3$ | $CH_3$ | 2-F, 4-$NO_2$, 5-$OCH_3$ | |
| 2.65 | N | N | $CCl_3$ | $CH_2CH_2Ph$ | H | |
| 2.66 | N | N | $CCl_3$ | $CH_2CH_2Ph$ | 2-F | |
| 2.67 | N | N | $CCl_3$ | $CH_2CH_2Ph$ | 2-Cl | |
| 2.68 | N | N | $CCl_3$ | $CH_2CH_2Ph$ | 4-F | |
| 2.69 | N | N | $CCl_3$ | $CH_2CH_2Ph$ | 4-Cl | |
| 2.70 | N | N | $CCl_3$ | $CH_2CH_2Ph$ | 2,4-$F_2$ | |
| 2.71 | N | N | $CCl_3$ | $CH_2CH_2Ph$ | 2,4-$Cl_2$ | |
| 2.72 | N | N | $CCl_3$ | $CH_2CH_2Ph$ | 2-F, 4-$NO_2$, 5-$OCH_3$ | |
| 2.73 | N | N | Ph | H | H | |
| 2.74 | N | N | Ph | H | 2-F | |
| 2.75 | N | N | Ph | H | 2-Cl | |
| 2.76 | N | N | Ph | H | 4-F | |
| 2.77 | N | N | Ph | H | 4-Cl | |
| 2.78 | N | N | Ph | H | 2,4-$F_2$ | |
| 2.79 | N | N | Ph | H | 2,4-$Cl_2$ | |
| 2.80 | N | N | Ph | H | 2-F, 4-$NO_2$, 5-$OCH_3$ | |
| 2.81 | N | N | Ph | $CH_3$ | H | |
| 2.82 | N | N | Ph | $CH_3$ | 2-F | |
| 2.83 | N | N | Ph | $CH_3$ | 2-Cl | |
| 2.84 | N | N | Ph | $CH_3$ | 4-F | |
| 2.85 | N | N | Ph | $CH_3$ | 4-Cl | |
| 2.86 | N | N | Ph | $CH_3$ | 2,4-$F_2$ | |
| 2.87 | N | N | Ph | $CH_3$ | 2,4-$Cl_2$ | |
| 2.88 | N | N | Ph | $CH_3$ | 2-F, 4-$NO_2$, 5-$OCH_3$ | |
| 2.89 | N | N | Ph | $CH_2CH_2Ph$ | H | |
| 2.90 | N | N | Ph | $CH_2CH_2Ph$ | 2-F | |
| 2.91 | N | N | Ph | $CH_2CH_2Ph$ | 2-Cl | |
| 2.92 | N | N | Ph | $CH_2CH_2Ph$ | 4-F | |
| 2.93 | N | N | Ph | $CH_2CH_2Ph$ | 4-Cl | |
| 2.94 | N | N | Ph | $CH_2CH_2Ph$ | 2,4-$F_2$ | |
| 2.95 | N | N | Ph | $CH_2CH_2Ph$ | 2,4-$Cl_2$ | |
| 2.96 | N | N | Ph | $CH_2CH_2Ph$ | 2-F, 4-$NO_2$, 5-$OCH_3$ | |
| 2.97 | N | C(CN) | Cl | H | H | |
| 2.98 | N | C(CN) | Cl | H | 2-F | |
| 2.99 | N | C(CN) | Cl | H | 2-Cl | |
| 2.100 | N | C(CN) | Cl | H | 4-F | |
| 2.101 | N | C(CN) | Cl | H | 4-Cl | |
| 2.102 | N | C(CN) | Cl | H | 2,4-$F_2$ | |
| 2.103 | N | C(CN) | Cl | H | 2,4-$Cl_2$ | |
| 2.104 | N | C(CN) | Cl | H | 2-F, 4-$NO_2$, 5-$OCH_3$ | |
| 2.105 | N | C(CN) | Cl | $CH_3$ | H | |
| 2.106 | N | C(CN) | Cl | $CH_3$ | 2-F | |

TABLE 2-continued

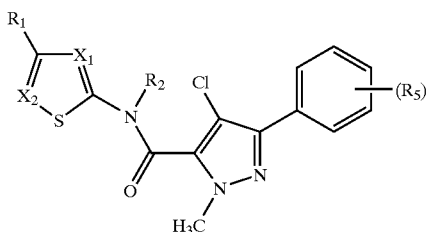

| Nr. | X₁ | X₂ | R₁ | R₂ | (R₅) | phys. data |
|---|---|---|---|---|---|---|
| 2.107 | N | C(CN) | Cl | CH₃ | 2-Cl | |
| 2.108 | N | C(CN) | Cl | CH₃ | 4-F | |
| 2.109 | N | C(CN) | Cl | CH₃ | 4-Cl | |
| 2.110 | N | C(CN) | Cl | CH₃ | 2,4-F₂ | |
| 2.111 | N | C(CN) | Cl | CH₃ | 2,4-Cl₂ | |
| 2.112 | N | C(CN) | Cl | CH₃ | 2-F, 4-NO₂, 5-OCH₃ | |
| 2.113 | N | C(CN) | Cl | CH₂CH₂Ph | H | |
| 2.114 | N | C(CN) | Cl | CH₂CH₂Ph | 2-F | |
| 2.115 | N | C(CN) | Cl | CH₂CH₂Ph | 2-Cl | |
| 2.116 | N | C(CN) | Cl | CH₂CH₂Ph | 4-F | |
| 2.117 | N | C(CN) | Cl | CH₂CH₂Ph | 4-Cl | |
| 2.118 | N | C(CN) | Cl | CH₂CH₂Ph | 2,4-F₂ | |
| 2.119 | N | C(CN) | Cl | CH₂CH₂Ph | 2,4-Cl₂ | |
| 2.120 | N | C(CN) | Cl | CH₂CH₂Ph | 2-F, 4-NO₂, 5-OCH₃ | |
| 2.121 | N | C(CN) | CF₃ | H | H | |
| 2.122 | N | C(CN) | CF₃ | H | 2-F | |
| 2.123 | N | C(CN) | CF₃ | H | 2-Cl | |
| 2.124 | N | C(CN) | CF₃ | H | 4-F | |
| 2.125 | N | C(CN) | CF₃ | H | 4-Cl | |
| 2.126 | N | C(CN) | CF₃ | H | 2,4-F₂ | |
| 2.127 | N | C(CN) | CF₃ | H | 2,4-Cl₂ | |
| 2.128 | N | C(CN) | CF₃ | H | 2-F, 4-NO₂, 5-OCH₃ | |
| 2.129 | N | C(CN) | CF₃ | CH₃ | H | |
| 2.130 | N | C(CN) | CF₃ | CH₃ | 2-F | |
| 2.131 | N | C(CN) | CF₃ | CH₃ | 2-Cl | |
| 2.132 | N | C(CN) | CF₃ | CH₃ | 4-F | |
| 2.133 | N | C(CN) | CF₃ | CH₃ | 4-Cl | |
| 2.134 | N | C(CN) | CF₃ | CH₃ | 2,4-F₂ | |
| 2.135 | N | C(CN) | CF₃ | CH₃ | 2,4-Cl₂ | |
| 2.136 | N | C(CN) | CF₃ | CH₃ | 2-F, 4-NO₂, 5-OCH₃ | |
| 2.137 | N | C(CN) | CF₃ | CH₂CH₂Ph | H | |
| 2.138 | N | C(CN) | CF₃ | CH₂CH₂Ph | 2-F | |
| 2.139 | N | C(CN) | CF₃ | CH₂CH₂Ph | 2-Cl | |
| 2.140 | N | C(CN) | CF₃ | CH₂CH₂Ph | 4-F | |
| 2.141 | N | C(CN) | CF₃ | CH₂CH₂Ph | 4-Cl | |
| 2.142 | N | C(CN) | CF₃ | CH₂CH₂Ph | 2,4-F₂ | |
| 2.143 | N | C(CN) | CF₃ | CH₂CH₂Ph | 2,4-Cl₂ | |
| 2.144 | N | C(CN) | CF₃ | CH₂CH₂Ph | 2-F, 4-NO₂, 5-OCH₃ | |
| 2.145 | N | C(CN) | CCl₃ | H | H | |
| 2.146 | N | C(CN) | CCl₃ | H | 2-F | |
| 2.147 | N | C(CN) | CCl₃ | H | 2-Cl | |
| 2.148 | N | C(CN) | CCl₃ | H | 4-F | |
| 2.149 | N | C(CN) | CCl₃ | H | 4-Cl | |
| 2.150 | N | C(CN) | CCl₃ | H | 2,4-F₂ | |
| 2.151 | N | C(CN) | CCl₃ | H | 2,4-Cl₂ | |
| 2.152 | N | C(CN) | CCl₃ | H | 2-F, 4-NO₂, 5-OCH₃ | |
| 2.153 | N | C(CN) | CCl₃ | CH₃ | H | |
| 2.154 | N | C(CN) | CCl₃ | CH₃ | 2-F | |
| 2.155 | N | C(CN) | CCl₃ | CH₃ | 2-Cl | |
| 2.156 | N | C(CN) | CCl₃ | CH₃ | 4-F | |
| 2.157 | N | C(CN) | CCl₃ | CH₃ | 4-Cl | |
| 2.158 | N | C(CN) | CCl₃ | CH₃ | 2,4-F₂ | |
| 2.159 | N | C(CN) | CCl₃ | CH₃ | 2,4-Cl₂ | |
| 2.160 | N | C(CN) | CCl₃ | CH₃ | 2-F, 4-NO₂, 5-OCH₃ | |
| 2.161 | N | C(CN) | CCl₃ | CH₂CH₂Ph | H | |
| 2.162 | N | C(CN) | CCl₃ | CH₂CH₂Ph | 2-F | |
| 2.163 | N | C(CN) | CCl₃ | CH₂CH₂Ph | 2-Cl | |
| 2.164 | N | C(CN) | CCl₃ | CH₂CH₂Ph | 4-F | |
| 2.165 | N | C(CN) | CCl₃ | CH₂CH₂Ph | 4-Cl | |
| 2.166 | N | C(CN) | CCl₃ | CH₂CH₂Ph | 2,4-F₂ | |
| 2.167 | N | C(CN) | CCl₃ | CH₂CH₂Ph | 2,4-Cl₂ | |
| 2.168 | N | C(CN) | CCl₃ | CH₂CH₂Ph | 2-F, 4-NO₂, 5-OCH₃ | |
| 2.169 | N | C(CN) | Ph | H | H | |
| 2.170 | N | C(CN) | Ph | H | 2-F | |

TABLE 2-continued

| Nr. | $X_1$ | $X_2$ | $R_1$ | $R_2$ | $(R_5)$ | phys. data |
|---|---|---|---|---|---|---|
| 2.171 | N | C(CN) | Ph | H | 2-Cl | |
| 2.172 | N | C(CN) | Ph | H | 4-F | |
| 2.173 | N | C(CN) | Ph | H | 4-Cl | |
| 2.174 | N | C(CN) | Ph | H | 2,4-$F_2$ | |
| 2.175 | N | C(CN) | Ph | H | 2,4-$Cl_2$ | |
| 2.176 | N | C(CN) | Ph | H | 2-F, 4-$NO_2$, 5-$OCH_3$ | |
| 2.177 | N | C(CN) | Ph | $CH_3$ | H | |
| 2.178 | N | C(CN) | Ph | $CH_3$ | 2-F | |
| 2.179 | N | C(CN) | Ph | $CH_3$ | 2-Cl | |
| 2.180 | N | C(CN) | Ph | $CH_3$ | 4-F | |
| 2.181 | N | C(CN) | Ph | $CH_3$ | 4-Cl | |
| 2.182 | N | C(CN) | Ph | $CH_3$ | 2,4-$F_2$ | |
| 2.183 | N | C(CN) | Ph | $CH_3$ | 2,4-$Cl_2$ | |
| 2.184 | N | C(CN) | Ph | $CH_3$ | 2-F, 4-$NO_2$, 5-$OCH_3$ | |
| 2.185 | N | C(CN) | Ph | $CH_2CH_2Ph$ | H | |
| 2.186 | N | C(CN) | Ph | $CH_2CH_2Ph$ | 2-F | |
| 2.187 | N | C(CN) | Ph | $CH_2CH_2Ph$ | 2-Cl | |
| 2.188 | N | C(CN) | Ph | $CH_2CH_2Ph$ | 4-F | |
| 2.189 | N | C(CN) | Ph | $CH_2CH_2Ph$ | 4-Cl | |
| 2.190 | N | C(CN) | Ph | $CH_2CH_2Ph$ | 2,4-$F_2$ | |
| 2.191 | N | C(CN) | Ph | $CH_2CH_2Ph$ | 2,4-$Cl_2$ | |
| 2.192 | N | C(CN) | Ph | $CH_2CH_2Ph$ | 2-F, 4-$NO_2$, 5-$OCH_3$ | |
| 2.193 | C(CN) | N | Cl | H | H | |
| 2.194 | C(CN) | N | Cl | H | 2-F | |
| 2.195 | C(CN) | N | Cl | H | 2-Cl | |
| 2.196 | C(CN) | N | Cl | H | 4-F | |
| 2.197 | C(CN) | N | Cl | H | 4-Cl | |
| 2.198 | C(CN) | N | Cl | H | 2,4-$F_2$ | |
| 2.199 | C(CN) | N | Cl | H | 2,4-$Cl_2$ | |
| 2.200 | C(CN) | N | Cl | H | 2-F, 4-$NO_2$, 5-$OCH_3$ | |
| 2.201 | C(CN) | N | Cl | $CH_3$ | H | |
| 2.202 | C(CN) | N | Cl | $CH_3$ | 2-F | |
| 2.203 | C(CN) | N | Cl | $CH_3$ | 2-Cl | |
| 2.204 | C(CN) | N | Cl | $CH_3$ | 4-F | |
| 2.205 | C(CN) | N | Cl | $CH_3$ | 4-Cl | |
| 2.206 | C(CN) | N | Cl | $CH_3$ | 2,4-$F_2$ | |
| 2.207 | C(CN) | N | Cl | $CH_3$ | 2,4-$Cl_2$ | |
| 2.208 | C(CN) | N | Cl | $CH_3$ | 2-F, 4-$NO_2$, 5-$OCH_3$ | |
| 2.209 | C(CN) | N | Cl | $CH_2CH_2Ph$ | H | |
| 2.210 | C(CN) | N | Cl | $CH_2CH_2Ph$ | 2-F | |
| 2.211 | C(CN) | N | Cl | $CH_2CH_2Ph$ | 2-Cl | |
| 2.212 | C(CN) | N | Cl | $CH_2CH_2Pb$ | 4-F | |
| 2.213 | C(CN) | N | Cl | $CH_2CH_2Ph$ | 4-Cl | |
| 2.214 | C(CN) | N | Cl | $CH_2CH_2Ph$ | 2,4-$F_2$ | |
| 2.215 | C(CN) | N | Cl | $CH_2CH_2Ph$ | 2,4-$Cl_2$ | |
| 2.216 | C(CN) | N | Cl | $CH_2CH_2Ph$ | 2-F, 4-$NO_2$, 5-$OCH_3$ | |
| 2.217 | C(CN) | N | $CF_3$ | H | H | |
| 2.218 | C(CN) | N | $CF_3$ | H | 2-F | |
| 2.219 | C(CN) | N | $CF_3$ | H | 2-Cl | |
| 2.220 | C(CN) | N | $CF_3$ | H | 4-F | |
| 2.221 | C(CN) | N | $CF_3$ | H | 4-Cl | |
| 2.222 | C(CN) | N | $CF_3$ | H | 2,4-$F_2$ | |
| 2.223 | C(CN) | N | $CF_3$ | H | 2,4-$Cl_2$ | |
| 2.224 | C(CN) | N | $CF_3$ | H | 2-F, 4-$NO_2$, 5-$OCH_3$ | |
| 2.225 | C(CN) | N | $CF_3$ | $CH_3$ | H | |
| 2.226 | C(CN) | N | $CF_3$ | $CH_3$ | 2-F | |
| 2.227 | C(CN) | N | $CF_3$ | $CH_3$ | 2-Cl | |
| 2.228 | C(CN) | N | $CF_3$ | $CH_3$ | 4-F | |
| 2.229 | C(CN) | N | $CF_3$ | $CH_3$ | 4-Cl | |
| 2.230 | C(CN) | N | $CF_3$ | $CH_3$ | 2,4-$F_2$ | |
| 2.231 | C(CN) | N | $CF_3$ | $CH_3$ | 2,4-$Cl_2$ | |
| 2.232 | C(CN) | N | $CF_3$ | $CH_3$ | 2-F, 4-$NO_2$, 5-$OCH_3$ | |
| 2.233 | C(CN) | N | $CF_3$ | $CH_2CH_2Ph$ | H | |
| 2.234 | C(CN) | N | $CF_3$ | $CH_2CH_2Ph$ | 2-F | |

TABLE 2-continued

| Nr. | X₁ | X₂ | R₁ | R₂ | (R₅) | phys. data |
|---|---|---|---|---|---|---|
| 2.235 | C(CN) | N | CF₃ | CH₂CH₂Ph | 2-Cl | |
| 2.236 | C(CN) | N | CF₃ | CH₂CH₂Ph | 4-F | |
| 2.237 | C(CN) | N | CF₃ | CH₂CH₂Ph | 4-Cl | |
| 2.238 | C(CN) | N | CF₃ | CH₂CH₂Ph | 2,4-F₂ | |
| 2.239 | C(CN) | N | CF₃ | CH₂CH₂Ph | 2,4-Cl₂ | |
| 2.240 | C(CN) | N | CF₃ | CH₂CH₂Ph | 2-F, 4-NO₂, 5-OCH₃ | |
| 2.241 | C(CN) | N | CCl₃ | H | H | |
| 2.242 | C(CN) | N | CCl₃ | H | 2-F | |
| 2.243 | C(CN) | N | CCl₃ | H | 2-Cl | |
| 2.244 | C(CN) | N | CCl₃ | H | 4-F | |
| 2.245 | C(CN) | N | CCl₃ | H | 4-Cl | |
| 2.246 | C(CN) | N | CCl₃ | H | 2,4-F₂ | |
| 2.247 | C(CN) | N | CCl₃ | H | 2,4-Cl₂ | |
| 2.248 | C(CN) | N | CCl₃ | H | 2-F, 4-NO₂, 5-OCH₃ | |
| 2.249 | C(CN) | N | CCl₃ | CH₃ | H | |
| 2.250 | C(CN) | N | CCl₃ | CH₃ | 2-F | |
| 2.251 | C(CN) | N | CCl₃ | CH₃ | 2-Cl | |
| 2.252 | C(CN) | N | CCl₃ | CH₃ | 4-F | |
| 2.253 | C(CN) | N | CCl₃ | CH₃ | 4-Cl | |
| 2.254 | C(CN) | N | CCl₃ | CH₃ | 2,4-F₂ | |
| 2.255 | C(CN) | N | CCl₃ | CH₃ | 2,4-Cl₂ | |
| 2.256 | C(CN) | N | CCl₃ | CH₃ | 2-F, 4-NO₂, 5-OCH₃ | |
| 2.257 | C(CN) | N | CCl₃ | CH₂CH₂Ph | H | |
| 2.258 | C(CN) | N | CCl₃ | CH₂CH₂Ph | 2-F | |
| 2.259 | C(CN) | N | CCl₃ | CH₂CH₂Ph | 2-Cl | |
| 2.260 | C(CN) | N | CCl₃ | CH₂CH₂Ph | 4-F | |
| 2.261 | C(CN) | N | CCl₃ | CH₂CH₂Ph | 4-Cl | |
| 2.262 | C(CN) | N | CCl₃ | CH₂CH₂Ph | 2,4-F₂ | |
| 2.263 | C(CN) | N | CCl₃ | CH₂CH₂Ph | 2,4-Cl₂ | |
| 2.264 | C(CN) | N | CCl₃ | CH₂CH₂Ph | 2-F, 4-NO₂, 5-OCH₃ | |
| 2.265 | C(CN) | N | Ph | H | H | |
| 2.266 | C(CN) | N | Ph | H | 2-F | |
| 2.267 | C(CN) | N | Ph | H | 2-Cl | |
| 2.268 | C(CN) | N | Ph | H | 4-F | |
| 2.269 | C(CN) | N | Ph | H | 4-Cl | |
| 2.270 | C(CN) | N | Ph | H | 2,4-F₂ | |
| 2.271 | C(CN) | N | Ph | H | 2,4-Cl₂ | |
| 2.272 | C(CN) | N | Ph | H | 2-F, 4-NO₂, 5-OCH₃ | |
| 2.273 | C(CN) | N | Ph | CH₃ | H | |
| 2.274 | C(CN) | N | Ph | CH₃ | 2-F | |
| 2.275 | C(CN) | N | Ph | CH₃ | 2-Cl | |
| 2.276 | C(CN) | N | Ph | CH₃ | 4-F | |
| 2.277 | C(CN) | N | Ph | CH₃ | 4-Cl | |
| 2.278 | C(CN) | N | Ph | CH₃ | 2,4-F₂ | |
| 2.279 | C(CN) | N | Ph | CH₃ | 2,4-Cl₂ | |
| 2.280 | C(CN) | N | Ph | CH₃ | 2-F, 4-NO₂, 5-OCH₃ | |
| 2.281 | C(CN) | N | Ph | CH₂CH₂Ph | H | |
| 2.282 | C(CN) | N | Ph | CH₂CH₂Ph | 2-F | |
| 2.283 | C(CN) | N | Ph | CH₂CH₂Ph | 2-Cl | |
| 2.284 | C(CN) | N | Ph | CH₂CH₂Ph | 4-F | |
| 2.285 | C(CN) | N | Ph | CH₂CH₂Ph | 4-Cl | |
| 2.286 | C(CN) | N | Ph | CH₂CH₂Ph | 2,4-F₂ | |
| 2.287 | C(CN) | N | Ph | CH₂CH₂Ph | 2,4-Cl₂ | |
| 2.288 | C(CN) | N | Ph | CH₂CH₂Ph | 2-F, 4-NO₂, 5-OCH₃ | |
| 2.289 | C(CN) | C(CN) | Cl | H | H | |
| 2.290 | C(CN) | C(CN) | Cl | H | 2-F | |
| 2.291 | C(CN) | C(CN) | Cl | H | 2-Cl | |
| 2.292 | C(CN) | C(CN) | Cl | H | 4-F | |
| 2.293 | C(CN) | C(CN) | Cl | H | 4-Cl | |
| 2.294 | C(CN) | C(CN) | Cl | H | 2,4-F₂ | |
| 2.295 | C(CN) | C(CN) | Cl | H | 2,4-Cl₂ | |
| 2.296 | C(CN) | C(CN) | Cl | H | 2-F, 4-NO₂, 5-OCH₃ | |
| 2.297 | C(CN) | C(CN) | Cl | CH₃ | H | |
| 2.298 | C(CN) | C(CN) | Cl | CH₃ | 2-F | |

TABLE 2-continued

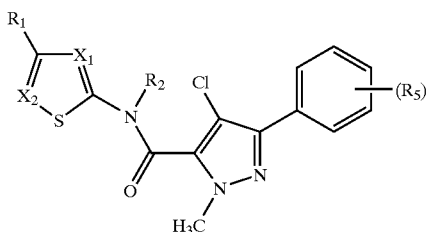

| Nr. | $X_1$ | $X_2$ | $R_1$ | $R_2$ | ($R_5$) | phys. data |
|---|---|---|---|---|---|---|
| 2.299 | C(CN) | C(CN) | Cl | $CH_3$ | 2-Cl | |
| 2.300 | C(CN) | C(CN) | Cl | $CH_3$ | 4-F | |
| 2.301 | C(CN) | C(CN) | Cl | $CH_3$ | 4-Cl | |
| 2.302 | C(CN) | C(CN) | Cl | $CH_3$ | 2,4-$F_2$ | |
| 2.303 | C(CN) | C(CN) | Cl | $CH_3$ | 2,4-$Cl_2$ | |
| 2.304 | C(CN) | C(CN) | Cl | $CH_3$ | 2-F, 4-$NO_2$, 5-$OCH_3$ | |
| 2.305 | C(CN) | C(CN) | Cl | $CH_2CH_2Ph$ | H | |
| 2.306 | C(CN) | C(CN) | Cl | $CH_2CH_2Ph$ | 2-F | |
| 2.307 | C(CN) | C(CN) | Cl | $CH_2CH_2Ph$ | 2-Cl | |
| 2.308 | C(CN) | C(CN) | Cl | $CH_2CH_2Ph$ | 4-F | |
| 2.309 | C(CN) | C(CN) | Cl | $CH_2CH_2Ph$ | 4-Cl | |
| 2.310 | C(CN) | C(CN) | Cl | $CH_2CH_2Ph$ | 2,4-$F_2$ | |
| 2.311 | C(CN) | C(CN) | Cl | $CH_2CH_2Ph$ | 2,4-$Cl_2$ | |
| 2.312 | C(CN) | C(CN) | Cl | $CH_2CH_2Ph$ | 2-F, 4-$NO_2$, 5-$CH_3$ | |
| 2.313 | C(CN) | C(CN) | $CF_3$ | H | H | |
| 2.314 | C(CN) | C(CN) | $CF_3$ | H | 2-F | |
| 2.315 | C(CN) | C(CN) | $CF_3$ | H | 2-Cl | |
| 2.316 | C(CN) | C(CN) | $CF_3$ | H | 4-F | |
| 2.317 | C(CN) | C(CN) | $CF_3$ | H | 4-Cl | |
| 2.318 | C(CN) | C(CN) | $CF_3$ | H | 2,4-$F_2$ | |
| 2.319 | C(CN) | C(CN) | $CF_3$ | H | 2,4-$Cl_2$ | |
| 2.320 | C(CN) | C(CN) | $CF_3$ | H | 2-F, 4-$NO_2$, 5-$OCH_3$ | |
| 2.321 | C(CN) | C(CN) | $CF_3$ | $CH_3$ | H | |
| 2.322 | C(CN) | C(CN) | $CF_3$ | $CH_3$ | 2-F | |
| 2.323 | C(CN) | C(CN) | $CF_3$ | $CH_3$ | 2-Cl | |
| 2.324 | C(CN) | C(CN) | $CF_3$ | $CH_3$ | 4-F | |
| 2.325 | C(CN) | C(CN) | $CF_3$ | $CH_3$ | 4-Cl | |
| 2.326 | C(CN) | C(CN) | $CF_3$ | $CH_3$ | 2,4-$F_2$ | |
| 2.327 | C(CN) | C(CN) | $CF_3$ | $CH_3$ | 2,4-$Cl_2$ | |
| 2.328 | C(CN) | C(CN) | $CF_3$ | $CH_3$ | 2-F, 4-$NO_2$, 5-$OCH_3$ | |
| 2.329 | C(CN) | C(CN) | $CF_3$ | $CH_2CH_2Ph$ | H | |
| 2.330 | C(CN) | C(CN) | $CF_3$ | $CH_2CH_2Ph$ | 2-F | |
| 2.331 | C(CN) | C(CN) | $CF_3$ | $CH_2CH_2Ph$ | 2-Cl | |
| 2.332 | C(CN) | C(CN) | $CF_3$ | $CH_2CH_2Ph$ | 4-F | |
| 2.333 | C(CN) | C(CN) | $CF_3$ | $CH_2CH_2Ph$ | 4-Cl | |
| 2.334 | C(CN) | C(CN) | $CF_3$ | $CH_2CH_2Ph$ | 2,4-$F_2$ | |
| 2.335 | C(CN) | C(CN) | $CF_3$ | $CH_2CH_2Ph$ | 2,4-$Cl_2$ | |
| 2.336 | C(CN) | C(CN) | $CF_3$ | $CH_2CH_2Ph$ | 2-F, 4-$NO_2$, 5-$OCH_3$ | |
| 2.337 | C(CN) | C(CN) | $CCl_3$ | H | H | |
| 2.338 | C(CN) | C(CN) | $CCl_3$ | H | 2-F | |
| 2.339 | C(CN) | C(CN) | $CCl_3$ | H | 2-Cl | |
| 2.340 | C(CN) | C(CN) | $CCl_3$ | H | 4-F | |
| 2.341 | C(CN) | C(CN) | $CCl_3$ | H | 4-Cl | |
| 2.342 | C(CN) | C(CN) | $CCl_3$ | H | 2,4-$F_2$ | |
| 2.343 | C(CN) | C(CN) | $CCl_3$ | H | 2,4-$Cl_2$ | |
| 2.344 | C(CN) | C(CN) | $CCl_3$ | H | 2-F, 4-$NO_2$, 5-$OCH_3$ | |
| 2.345 | C(CN) | C(CN) | $CCl_3$ | $CH_3$ | H | |
| 2.346 | C(CN) | C(CN) | $CCl_3$ | $CH_3$ | 2-F | |
| 2.347 | C(CN) | C(CN) | $CCl_3$ | $CH_3$ | 2-Cl | |
| 2.348 | C(CN) | C(CN) | $CCl_3$ | $CH_3$ | 4-F | |
| 2.349 | C(CN) | C(CN) | $CCl_3$ | $CH_3$ | 4-Cl | |
| 2.350 | C(CN) | C(CN) | $CCl_3$ | $CH_3$ | 2,4-$F_2$ | |
| 2.351 | C(CN) | C(CN) | $CCl_3$ | $CH_3$ | 2,4-$Cl_2$ | |
| 2.352 | C(CN) | C(CN) | $CCl_3$ | $CH_3$ | 2-F, 4-$NO_2$, 5-$OCH_3$ | |
| 2.353 | C(CN) | C(CN) | $CCl_3$ | $CH_2CH_2Ph$ | H | |
| 2.354 | C(CN) | C(CN) | $CCl_3$ | $CH_2CH_2Ph$ | 2-F | |
| 2.355 | C(CN) | C(CN) | $CCl_3$ | $CH_2CH_2Ph$ | 2-Cl | |
| 2.356 | C(CN) | C(CN) | $CCl_3$ | $CH_2CH_2Ph$ | 4-F | |
| 2.357 | C(CN) | C(CN) | $CCl_3$ | $CH_2CH_2Ph$ | 4-Cl | |
| 2.358 | C(CN) | C(CN) | $CCl_3$ | $CH_2CH_2Ph$ | 2,4-$F_2$ | |
| 2.359 | C(CN) | C(CN) | $CCl_3$ | $CH_2CH_2Ph$ | 2,4-$Cl_2$ | |
| 2.360 | C(CN) | C(CN) | $CCl_3$ | $CH_2CH_2Ph$ | 2-F, 4-$NO_2$, 5-$OCH_3$ | |
| 2.361 | C(CN) | C(CN) | Ph | H | H | |
| 2.362 | C(CN) | C(CN) | Ph | H | 2-F | |

TABLE 2-continued

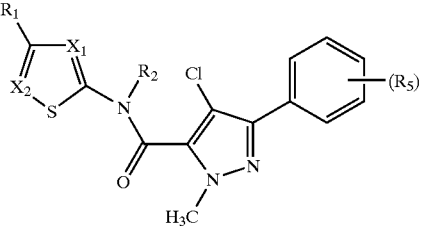

| Nr. | X$_1$ | X$_2$ | R$_1$ | R$_2$ | (R$_5$) | phys. data |
|---|---|---|---|---|---|---|
| 2.363 | C(CN) | C(CN) | Ph | H | 2-Cl | |
| 2.364 | C(CN) | C(CN) | Ph | H | 4-F | |
| 2.365 | C(CN) | C(CN) | Ph | H | 4-Cl | |
| 2.366 | C(CN) | C(CN) | Ph | H | 2,4-F$_2$ | |
| 2.367 | C(CN) | C(CN) | Ph | H | 2,4-Cl$_2$ | |
| 2.368 | C(CN) | C(CN) | Ph | H | 2-F, 4-NO$_2$, 5-OCH$_3$ | |
| 2.369 | C(CN) | C(CN) | Ph | CH$_3$ | H | |
| 2.370 | C(CN) | C(CN) | Ph | CH$_3$ | 2-F | |
| 2.371 | C(CN) | C(CN) | Ph | CH$_3$ | 2-Cl | |
| 2.372 | C(CN) | C(CN) | Ph | CH$_3$ | 4-F | |
| 2.373 | C(CN) | C(CN) | Ph | CH$_3$ | 4-Cl | |
| 2.374 | C(CN) | C(CN) | Ph | CH$_3$ | 2,4-F$_2$ | |
| 2.375 | C(CN) | C(CN) | Ph | CH$_3$ | 2,4-Cl$_2$ | |
| 2.376 | C(CN) | C(CN) | Ph | CH$_3$ | 2-F, 4-NO$_2$, 5-OCH$_3$ | |
| 2.377 | C(CN) | C(CN) | Ph | CH$_2$CH$_2$Ph | H | |
| 2.378 | C(CN) | C(CN) | Ph | CH$_2$CH$_2$Ph | 2-F | |
| 2.379 | C(CN) | C(CN) | Ph | CH$_2$CH$_2$Ph | 2-Cl | |
| 2.380 | C(CN) | C(CN) | Ph | CH$_2$CH$_2$Ph | 4-F | |
| 2.381 | C(CN) | C(CN) | Ph | CH$_2$CH$_2$Ph | 4-Cl | |
| 2.382 | C(CN) | C(CN) | Ph | CH$_2$CH$_2$Ph | 2,4-F$_2$ | |
| 2.383 | C(CN) | C(CN) | Ph | CH$_2$CH$_2$Ph | 2,4-Cl$_2$ | |
| 2.384 | C(CN) | C(CN) | Ph | CH$_2$CH$_2$Ph | 2-F, 4-NO$_2$, 5-OCH$_3$ | |

TABLE 3

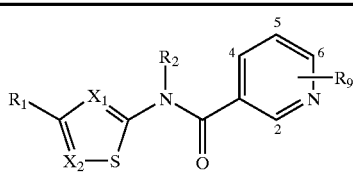

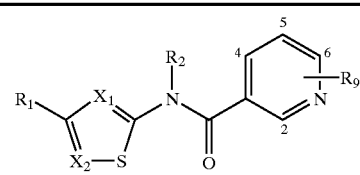

| Nr. | X$_1$ | X$_2$ | R$_1$ | R$_2$ | R$_9$ | phys. data |
|---|---|---|---|---|---|---|
| 3.1 | N | N | Cl | H | H | |
| 3.2 | N | N | Cl | H | 2-Cl | |
| 3.3 | N | N | Cl | H | 6-OCH$_3$ | |
| 3.4 | N | N | Cl | CH$_3$ | H | |
| 3.5 | N | N | Cl | CH$_3$ | 2-Cl | |
| 3.6 | N | N | Cl | CH$_3$ | 6-OCH$_3$ | |
| 3.7 | N | N | Cl | CH$_2$CH$_2$Ph | H | |
| 3.8 | N | N | Cl | CH$_2$CH$_2$Ph | 2-Cl | |
| 3.9 | N | N | Cl | CH$_2$CH$_2$Ph | 6-OCH$_3$ | |
| 3.10 | N | N | CF$_3$ | H | H | |
| 3.11 | N | N | CF$_3$ | H | 2-Cl | |
| 3.12 | N | N | CF$_3$ | H | 6-OCH$_3$ | |
| 3.13 | N | N | CF$_3$ | CH$_3$ | H | |
| 3.14 | N | N | CF$_3$ | CH$_3$ | 2-Cl | |
| 3.15 | N | N | CF$_3$ | CH$_3$ | 6-OCH$_3$ | |
| 3.16 | N | N | CF$_3$ | CH$_2$CH$_2$Ph | H | |
| 3.17 | N | N | CF$_3$ | CH$_2$CH$_2$Ph | 2-Cl | |
| 3.18 | N | N | CF$_3$ | CH$_2$CH$_2$Ph | 6-OCH$_3$ | |
| 3.19 | N | N | CCl$_3$ | H | H | |
| 3.20 | N | N | CCl$_3$ | H | 2-Cl | |
| 3.21 | N | N | CCl$_3$ | H | 6-OCH$_3$ | |
| 3.22 | N | N | CCl$_3$ | CH$_3$ | H | |
| 3.23 | N | N | CCl$_3$ | CH$_3$ | 2-Cl | |
| 3.24 | N | N | CCl$_3$ | CH$_3$ | 6-OCH$_3$ | |
| 3.25 | N | N | CCl$_3$ | CH$_2$CH$_2$Ph | H | |
| 3.26 | N | N | CCl$_3$ | CH$_2$CH$_2$Ph | 2-Cl | |
| 3.27 | N | N | CCl$_3$ | CH$_2$CH$_2$Ph | 6-OCH$_3$ | |
| 3.28 | N | N | Ph | H | H | |
| 3.29 | N | N | Ph | H | 2-Cl | |
| 3.30 | N | N | Ph | H | 6-OCH$_3$ | |
| 3.31 | N | N | Ph | CH$_3$ | H | |
| 3.32 | N | N | Ph | CH$_3$ | 2-Cl | |
| 3.33 | N | N | Ph | CH$_3$ | 6-OCH$_3$ | |
| 3.34 | N | N | Ph | CH$_2$CH$_2$Ph | H | |
| 3.35 | N | N | Ph | CH$_2$CH$_2$Ph | 2-Cl | |
| 3.36 | N | N | Ph | CH$_2$CH$_2$Ph | 6-OCH$_3$ | |
| 3.37 | N | C(CN) | Cl | H | H | |
| 3.38 | N | C(CN) | Cl | H | 2-Cl | |
| 3.39 | N | C(CN) | Cl | H | 6-OCH$_3$ | |
| 3.40 | N | C(CN) | Cl | CH$_3$ | H | |
| 3.41 | N | C(CN) | Cl | CH$_3$ | 2-Cl | |
| 3.42 | N | C(CN) | Cl | CH$_3$ | 6-OCH$_3$ | |
| 3.43 | N | C(CN) | Cl | CH$_2$CH$_2$Ph | H | |
| 3.44 | N | C(CN) | Cl | CH$_2$CH$_2$Ph | 2-Cl | |
| 3.45 | N | C(CN) | Cl | CH$_2$CH$_2$Ph | 6-OCH$_3$ | |
| 3.46 | N | C(CN) | CF$_3$ | H | H | |
| 3.47 | N | C(CN) | CF$_3$ | H | 2-Cl | |
| 3.48 | N | C(CN) | CF$_3$ | H | 6-OCH$_3$ | solid |
| 3.49 | N | C(CN) | CF$_3$ | CH$_3$ | H | |
| 3.50 | N | C(CN) | CF$_3$ | CH$_3$ | 2-Cl | |

TABLE 3-continued

| Nr. | $X_1$ | $X_2$ | $R_1$ | $R_2$ | $R_9$ | phys. data |
|---|---|---|---|---|---|---|
| 3.51 | N | C(CN) | $CF_3$ | $CH_3$ | 6-$OCH_3$ | |
| 3.52 | N | C(CN) | $CF_3$ | $CH_2CH_2Ph$ | H | |
| 3.53 | N | C(CN) | $CF_3$ | $CH_2CH_2Ph$ | 2-Cl | |
| 3.54 | N | C(CN) | $CF_3$ | $CH_2CH_2Ph$ | 6-$OCH_3$ | |
| 3.55 | N | C(CN) | $CCl_3$ | H | H | |
| 3.56 | N | C(CN) | $CCl_3$ | H | 2-Cl | |
| 3.57 | N | C(CN) | $CCl_3$ | H | 6-$OCH_3$ | |
| 3.58 | N | C(CN) | $CCl_3$ | $CH_3$ | H | |
| 3.59 | N | C(CN) | $CCl_3$ | $CH_3$ | 2-Cl | |
| 3.60 | N | C(CN) | $CCl_3$ | $CH_3$ | 6-$OCH_3$ | |
| 3.61 | N | C(CN) | $CCl_3$ | $CH_2CH_2Ph$ | H | |
| 3.62 | N | C(CN) | $CCl_3$ | $CH_2CH_2Ph$ | 2-Cl | |
| 3.63 | N | C(CN) | $CCl_3$ | $CH_2CH_2Ph$ | 6-$OCH_3$ | |
| 3.64 | N | C(CN) | Ph | H | H | |
| 3.65 | N | C(CN) | Ph | H | 2-Cl | |
| 3.66 | N | C(CN) | Ph | H | 6-$OCH_3$ | |
| 3.67 | N | C(CN) | Ph | $CH_3$ | H | |
| 3.68 | N | C(CN) | Ph | $CH_3$ | 2-Cl | |
| 3.69 | N | C(CN) | Ph | $CH_3$ | 6-$OCH_3$ | |
| 3.70 | N | C(CN) | Ph | $CH_2CH_2Ph$ | H | |
| 3.71 | N | C(CN) | Ph | $CH_2CH_2Ph$ | 2-Cl | |
| 3.72 | N | C(CN) | Ph | $CH_2CH_2Ph$ | 6-$OCH_3$ | |
| 3.73 | C(CN) | N | Cl | H | H | |
| 3.74 | C(CN) | N | Cl | H | 2-Cl | |
| 3.75 | C(CN) | N | Cl | H | 6-$OCH_3$ | |
| 3.76 | C(CN) | N | Cl | $CH_3$ | H | |
| 3.77 | C(CN) | N | Cl | $CH_3$ | 2-Cl | |
| 3.78 | C(CN) | N | Cl | $CH_3$ | 6-$OCH_3$ | |
| 3.79 | C(CN) | N | Cl | $CH_2CH_2Ph$ | H | |
| 3.80 | C(CN) | N | Cl | $CH_2CH_2Ph$ | 2-Cl | |
| 3.81 | C(CN) | N | Cl | $CH_2CH_2Ph$ | 6-$OCH_3$ | |
| 3.82 | C(CN) | N | $CF_3$ | H | H | |
| 3.83 | C(CN) | N | $CF_3$ | H | 2-Cl | |
| 3.84 | C(CN) | N | $CF_3$ | H | 6-$OCH_3$ | |
| 3.85 | C(CN) | N | $CF_3$ | $CH_3$ | H | |
| 3.86 | C(CN) | N | $CF_3$ | $CH_3$ | 2-Cl | |
| 3.87 | C(CN) | N | $CF_3$ | $CH_3$ | 6-$OCH_3$ | |
| 3.88 | C(CN) | N | $CF_3$ | $CH_2CH_2Ph$ | H | |
| 3.89 | C(CN) | N | $CF_3$ | $CH_2CH_2Ph$ | 2-Cl | |
| 3.90 | C(CN) | N | $CF_3$ | $CH_2CH_2Ph$ | 6-$OCH_3$ | |
| 3.91 | C(CN) | N | $CCl_3$ | H | H | |
| 3.92 | C(CN) | N | $CCl_3$ | H | 2-Cl | |
| 3.93 | C(CN) | N | $CCl_3$ | H | 6-$OCH_3$ | |
| 3.94 | C(CN) | N | $CCl_3$ | $CH_3$ | H | |
| 3.95 | C(CN) | N | $CCl_3$ | $CH_3$ | 2-Cl | |
| 3.96 | C(CN) | N | $CCl_3$ | $CH_3$ | 6-$OCH_3$ | |
| 3.97 | C(CN) | N | $CCl_3$ | $CH_2CH_2Ph$ | H | |
| 3.98 | C(CN) | N | $CCl_3$ | $CH_2CH_2Ph$ | 2-Cl | |
| 3.99 | C(CN) | N | $CCl_3$ | $CH_2CH_2Ph$ | 6-$OCH_3$ | |
| 3.100 | C(CN) | N | Ph | H | H | |
| 3.101 | C(CN) | N | Ph | H | 2-Cl | |
| 3.102 | C(CN) | N | Ph | H | 6-$OCH_3$ | |
| 3.103 | C(CN) | N | Ph | $CH_3$ | H | |
| 3.104 | C(CN) | N | Ph | $CH_3$ | 2-Cl | |
| 3.105 | C(CN) | N | Ph | $CH_3$ | 6-$OCH_3$ | |
| 3.106 | C(CN) | N | Ph | $CH_2CH_2Ph$ | H | |
| 3.107 | C(CN) | N | Ph | $CH_2CH_2Ph$ | 2-Cl | |
| 3.108 | C(CN) | N | Ph | $CH_2CH_2Ph$ | 6-$OCH_3$ | |
| 3.109 | C(CN) | C(CN) | Cl | H | H | |
| 3.110 | C(CN) | C(CN) | Cl | H | 2-Cl | m.p. 226–7° |
| 3.111 | C(CN) | C(CN) | Cl | H | 6-$OCH_3$ | |
| 3.112 | C(CN) | C(CN) | Cl | $CH_3$ | H | |
| 3.113 | C(CN) | C(CN) | Cl | $CH_3$ | 2-Cl | |
| 3.114 | C(CN) | C(CN) | Cl | $CH_3$ | 6-$OCH_3$ | |
| 3.115 | C(CN) | C(CN) | Cl | $CH_2CH_2Ph$ | H | |
| 3.116 | C(CN) | C(CN) | Cl | $CH_2CH_2Ph$ | 2-Cl | |
| 3.117 | C(CN) | C(CN) | Cl | $CH_2CH_2Ph$ | 6-$OCH_3$ | |
| 3.118 | C(CN) | C(CN) | $CF_3$ | H | H | |
| 3.119 | C(CN) | C(CN) | $CF_3$ | H | 2-Cl | |
| 3.120 | C(CN) | C(CN) | $CF_3$ | H | 6-$OCH_3$ | |
| 3.121 | C(CN) | C(CN) | $CF_3$ | $CH_3$ | H | |
| 3.122 | C(CN) | C(CN) | $CF_3$ | $CH_3$ | 2-Cl | |
| 3.123 | C(CN) | C(CN) | $CF_3$ | $CH_3$ | 6-$OCH_3$ | |
| 3.124 | C(CN) | C(CN) | $CF_3$ | $CH_2CH_2Ph$ | H | |
| 3.125 | C(CN) | C(CN) | $CF_3$ | $CH_2CH_2Ph$ | 2-Cl | |
| 3.126 | C(CN) | C(CN) | $CF_3$ | $CH_2CH_2Ph$ | 6-$OCH_3$ | |
| 3.127 | C(CN) | C(CN) | $CCl_3$ | H | H | |
| 3.128 | C(CN) | C(CN) | $CCl_3$ | H | 2-Cl | |
| 3.129 | C(CN) | C(CN) | $CCl_3$ | H | 6-$OCH_3$ | |
| 3.130 | C(CN) | C(CN) | $CCl_3$ | $CH_3$ | H | |
| 3.131 | C(CN) | C(CN) | $CCl_3$ | $CH_3$ | 2-Cl | |
| 3.132 | C(CN) | C(CN) | $CCl_3$ | $CH_3$ | 6-$OCH_3$ | |
| 3.133 | C(CN) | C(CN) | $CCl_3$ | $CH_2CH_2Ph$ | H | |
| 3.134 | C(CN) | C(CN) | $CCl_3$ | $CH_2CH_2Ph$ | 2-Cl | |
| 3.135 | C(CN) | C(CN) | $CCl_3$ | $CH_2CH_2Ph$ | 6-$OCH_3$ | |
| 3.136 | C(CN) | C(CN) | Ph | H | H | |
| 3.137 | C(CN) | C(CN) | Ph | H | 2-Cl | |
| 3.138 | C(CN) | C(CN) | Ph | H | 6-$OCH_3$ | |
| 3.139 | C(CN) | C(CN) | Ph | $CH_3$ | H | |
| 3.140 | C(CN) | C(CN) | Ph | $CH_3$ | 2-Cl | |
| 3.141 | C(CN) | C(CN) | Ph | $CH_3$ | 6-$OCH_3$ | |
| 3.142 | C(CN) | C(CN) | Ph | $CH_2CH_2Ph$ | H | |
| 3.143 | C(CN) | C(CN) | Ph | $CH_2CH_2Ph$ | 2-Cl | |
| 3.144 | C(CN) | C(CN) | Ph | $CH_2CH_2Ph$ | 6-$OCH_3$ | |

Biological Examples

1. In vivo Test Against *Trichostrongylus colubriformis* and *Haemonchus contortus* in Mongolian gerbils (*Meriones unguiculatus*), Subcutaneous Injection Six- to eight-week old *Mongolian gerbils* are infected, using synthetic feed, with in each case about 2000 larvae of the 3rd stage of *T. colubriformis* and *H. contortus*. Six days after the infection, the gerbils are anaesthetized slightly using $N_2O$ and are treated by subcutaneous injection into the neck region with the test compounds, dissolved in a mixture of 2 parts of DMSO and 1 part of polyethylene glycol 400, with quantities of 100, 32 and 10–0.1 mg/kg. On day 9 (3 days after the treatment), when most of the H. contortus larvae of the late 4th stage and most of the *T. colubriformis* which are still present are immature adults, the gerbils are sacrificed to count the worms. The activity is calculated in % reduction of the number of worms in each gerbil by comparison with the geometric mean of the number of worms of infected and untreated gerbils.

In this test, a strong reduction of the nematode infestation is obtained using compounds of the formula I.

When the active compound is administered orally, similar results are obtained.

2. Stomach Insecticide Effect Against *Spodoptera littoralis*

Potted cotton plants are sprayed in the 5-leaf stage with an acetone/water test solution comprising 1, 3, 12.5 or 50 ppm of the compound to be tested.

After the coating has dried on, the plants are populated with about 30 larvae ($L_1$ stage) of *Spodoptera littoralis*. For each test compound and each test species, two plants are used. The experiment is carried out at about 24° C. and 60% relative atmospheric humidity. Evaluations and intermediate evaluations for moribund animals, larvae and feeding damage are carried out after 24, 48 and 72 h.

Even at a concentration of active compound of 3 ppm, the compounds of the formula I effect a total kill after 24 h.

3. Activity Against Plant-damaging Acarides

OP-sensitive *Tetranychus urticae*

16 h prior to the experiment, leaf parts from a mass culture, infested by *T. urticae,* are placed onto the primary leaves of bean plants (*Phaseolus vulgaris*). The plants thus infested by all stages of mites are, after the piece of leaf has been removed, sprayed to run off point with a test solution comprising 0.2, 0.4 or 1.6 ppm of the compound to be tested. The temperature in the greenhouse cabin is about 25° C. After 7 days, the percentage of mobile stages (adults and nymphs) and the eggs present are evaluated using binoculars.

At a concentration of active compound of 0.4 ppm, the compounds of the formula I effected a total kill.

4. Activity Against $L_1$ Larvae of *Lucilia sericata*

1 ml of an aqueous suspension of the active substance to be tested are mixed at about 50° C. with 3 ml of special medium for breeding larvae, such that a homogeneous mixture with a content of active compound of 250 or 125 ppm is formed. About 30 Lucilia larvae ($L_1$) are placed into each test tube sample. After 4 days, the mortality rate is determined. At 250 ppm, the compounds of the formula I have an efficacy of 100%.

5. Acaricidal Action Against *Boophilus microlus* (Biarra Strain)

On a plate made of PVC, an adhesive strip is attached horizontally such that 10 female Boophilus microplus ticks (Biarra strain) which have sucked themselves full with blood can be attached by their backs in a row, next to each other. Using an injection needle, each tick is injected with 1 $\mu$l of a liquid which is a 1:1 mixture of polyethylene glycol and acetone in which a certain amount of active compound of 1, 0.1 or 0.01 $\mu$g per tick is dissolved. Control animals are given an active-compound-free injection. After the treatment, the animals are kept in an insectary under normal conditions at about 28° C. and 80% relative atmospheric humidity until oviposition has taken place and the larvae have hatched from the eggs of the control animals. The activity of a test substance is determined using the $IR_{90}$, i.e. the dose of active compound at which, even after 30 days, 9 out of 10 female ticks (=90%) lay eggs which have lost their hatchability, is determined.

The compounds of the formula I score an $IR_{90}$ of 0.1 $\mu$g.

6. In vitro Activity Against Fed Females of *Boophilus microplus* (BIARRA)

4×10 fed female ticks of the OP-resistant BIARRA strain are attached to an adhesive tape and covered for 1 h with a wad of cotton which had been drenched with an emulsion or suspension of the test compound in concentrations of in each case 500, 125, 31 and 8 ppm. After 28 days, evaluation is carried out for mortality, oviposition and hatching of larvae.

An indication of the efficacy of the test compounds is the number of females which die quickly, before laying eggs, survive for some time without laying eggs, lay eggs in which no embryos are formed, lay eggs in which embryos are formed from which no larvae hatch, and lay eggs in which embryos are formed from which usually larvae hatch within 26 to 27 days.

In this test, the compounds of the formula I effect a rapid kill of more than 80% of the female ticks.

7. Contact Activity on *Aphis craccivora*

Pea seedlings infected with all development stages of the aphid are sprayed with a solution of active compound prepared from an emulsion concentrate and comprising 50, 25 or 12.5 ppm of active compound. After 3 days, the experiment is evaluated for a figure of more than 80% of dead aphids or aphids which have dropped. Only at this activity, a preparation is classed as being effective.

At a concentration of 12.5 ppm, the compounds of the formula I effect a total kill (=100%).

8. Larvicide Activity Against *Aedes aegypti*

Such an amount of a 0.1% solution of the active compound in acetone is pipetted onto the surface of 150 ml of water in a container that concentrations of 10, 3.3 and 1.6 ppm are obtained. After the acetone has evaporated, the container is populated with about 30–40 3-day-old Aedas larvae. Mortality is examined after 1, 2 and 5 days.

In this test, at a concentration of 1.6 ppm, the compounds of the formula I effect a total kill of all larvae even after one day.

9. In vivo Activity Against Adult *Ctenocephalides felis* on Domestic Cats, Oral Treatment The test substances are administered orally in a gelatine capsule to the domestic cats, before or after feeding, the dose varying between 0.5 and 20 mg/kg. On days 1, 3, 7 and 10 after the treatment, in each case 100 fleas (about 50 male and about 50 female) are placed onto each cat, depending on the result of the previous flea infestation. The activity (in % reduction of the number of fleas) is based on the number of alive fleas which are found by combing for 10 minutes one day after each new flea infestation, the activity in per cent corresponding to the arithmetic mean of the number of alive fleas on the control animals minus the number of alive fleas on the treated animals, divided by the arithmetic mean of the number of alive fleas on the control animals and multiplied by 100.

The dying fleas found in the cat cages and by combing are collected and placed in an incubator at 28° C. and 70% relative atmospheric humidity, and the survival rate/ mortality is checked after 24 h. If the majority of the dying fleas is dead, the test compound is classed as a flea adulticide, if the majority survives, the test compound has "knock down" activity.

In this test, the compounds of the formula I effect a kill of at least 80% of the fleas.

10. In vivo Activity Against Adult *Ctenocephalides felis* on Domestic Cats, Spot-on Treatment The test substances are administered to the domestic cats as spot-on, the dose varying between 0.5 and 10 mg/kg. On days 1, 3, 7 and 10 after the treatment, in each case 100 fleas (about 50 male and about 50 female) are placed onto each cat, depending on the result of the previous flea infestation.

The activity (in % reduction of the number of fleas) is based on the number of alive fleas which are found by combing for 10 minutes one day after each new flea infestation, the activity in per cent corresponding to the arithmetic mean of the number of alive fleas on the control animals minus the number of alive fleas on the treated animals, divided by the arithmetic mean of the number of alive fleas on the control animals and multiplied by 100.

The dying fleas found in the cat cages and by combing are collected and placed in an incubator at 28° C. and 70% relative atmospheric humidity, and the survival rate/ mortality is checked after 24 h. If the majority of the dying fleas is dead, the test compound is classed as a flea adulticide, if the majority survives, the test compound has "knock down" activity.

In this test, after 35 days the compounds of the formula I effect a kill of more than 90% of the fleas.

11. In vitro Activity Against Nymphs of *Amblyomma hebraeum*

About 5 starving nymphs are placed into a polystyrene test tube containing 2 ml of the test compound in solution, suspension or emulsion.

After immersing for 10 minutes and vortexing for 2×10 seconds, the test tubes are closed with a thick wad of cotton and inverted. Once all of the liquid has been absorbed by the wad of cotton, the wad is pushed halfway up into the test tube, which is still inverted, such that most of the liquid is drained from the wad of cotton, flowing into a Petri dish below.

Until evaluation, the test tubes are then stored at room temperature in a room illuminated with daylight. After 14 days, the test tubes are immersed into a beaker of boiling water. If, as a reaction to the heat, the ticks begin to move, the test substance is considered to be inactive at the concentration examined, otherwise, the ticks are considered to be dead and the test substance to be active at the concentration examined. All substances are tested in a concentration range of from 0.1 to 100 ppm.

In this test, the compounds of the formula I effect a kill of more than 80% of the ticks.

12. Activity Against *Dermanyssus gallinae*

2 to 3 ml of a solution comprising 10 ppm of active compound and about 200 mites (*Dermanyssus gallinae*) of different development stages are placed into a glass vessel open at the top. The vessel is then closed with a wad of cotton, shaken for 10 minutes, until the mites have been wetted completely and then inverted briefly so that the remaining test solution can be absorbed by the cotton. After 3 days, the mortality of the mites is determined by counting the dead animals and is stated in per cent.

The compounds of the formula I show good activity against *Dermanyssus gallinae*.

13. Activity Against *Musca domestica*

A sugar cube is treated with a solution of the test substance such that the concentration of test substance in the sugar, after drying overnight, is 250 ppm. This treated cube, together with a wet wad of cotton and 10 adult Musca domestica of an OP resistant strain, is placed onto a dish made of aluminium, covered with a beaker and incubated at 25° C. After 24 hours, the mortality rate is determined.

In this test, the compounds of the formula I show good activity against *Musca domestica*.

What is claimed is:

1. A compound of the formula

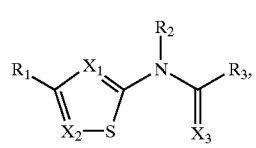

I in which $R_1$ is hydrogen, halogen, $C_1$–$C_6$alkyl, $C_1$–$C_6$alkoxy, $C_1$–$C_6$haloalkyl or unsubstituted or mono- to pentasubstituted phenyl, where the substituents are selected from the group consisting of $C_1$–$C_6$alkyl, $C_1$–$C_6$haloalkyl, $C_1$–$C_6$alkoxy, aryloxy, halogen, cyano and nitro, where, if the number of substituents exceeds 1, the substituents can be identical or different;

$R_2$ is hydrogen, $C_1$–$C_6$alkyl, ($C_1$–$C_6$alkylene)phenyl, pyridyl, $COOR_6$, $CONR_7R_8$, $COR_6$, allyl or $CH_2$—O—$R_6$;

$R_3$ is unsubstituted or substituted heterocyclyl, where the substituents are in each case selected from the group consisting of unsubstituted or substituted phenyl, where the substituents are selected from the group consisting of $C_1$–$C_6$alkyl, $C_1$–$C_6$alkoxy, halogen, cyano and nitro, where, if the number of substituents exceeds 1, the substituents can be identical or different, benzyl, $C_1$–$C_6$alkyl, $C_1$–$C_6$haloalkyl, $C_1$–$C_6$alkoxy, aryloxy, halogen, cyano, hydroxyl, amino and nitro, where, if the number of substituents exceeds 1, the substituents can be identical or different;

$R_6$ is $C_1$–$C_6$alkyl, phenyl or benzyl;

$R_7$ and $R_8$ independently of one another are hydrogen or $C_1$–$C_6$alkyl;

$X_1$ is N; $X_2$ is N; and $X_3$ is O or S.

2. A process for preparing compounds of the formula I according to claim 1, which comprises reacting a compound of the formula

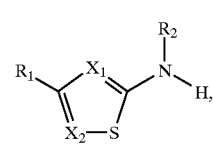

II which is known or can be prepared analogously to corresponding known compounds and in which $R_1$, $R_2$, $X_1$ and $X_2$ are as defined for formula I, with a compound of the formula

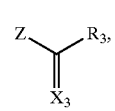

III which is known or can be prepared analogously to corresponding known compounds and in which $X_3$ and $R_3$ are as defined for formula I and Z is a leaving group, if appropriate in the presence of a basic catalyst, and in each case, if desired, converting a compound of the formula I obtainable by the process or in another manner, or an enantiomer thereof, into another compound of the formula I or an enantiomer thereof, separating an enantiomer mixture obtainable by the process and isolating the desired enantiomer.

3. A composition for controlling pests, which comprises, in addition to carriers and/or dispersants, at least one compound of the formula I according to claim 1 as active substance.

4. A method for controlling pests, which comprises applying a pesticidally effective amount of at least one compound of the formula I according to claim 1 to the pests or their habitat.

5. The method according to claim 4, wherein the pests are parasites on warm-blooded animals.

* * * * *